United States Patent
Barak et al.

(10) Patent No.: US 10,702,226 B2
(45) Date of Patent: Jul. 7, 2020

(54) SYSTEM AND METHOD FOR LOCAL THREE DIMENSIONAL VOLUME RECONSTRUCTION USING A STANDARD FLUOROSCOPE

(71) Applicant: Covidien LP, Mansfield, MA (US)

(72) Inventors: Ron Barak, Tel Aviv-Jaffa (IL); Oren P. Weingarten, Herzliya (IL); Ariel Birenbaum, Herzliya (IL); Guy Alexandroni, Ramat HaSharon (IL)

(73) Assignee: COVIDIEN LP, Mansfield, MA (US)

( * ) Notice: Subject to any disclaimer, the term of this patent is extended or adjusted under 35 U.S.C. 154(b) by 154 days.

(21) Appl. No.: 15/892,053

(22) Filed: Feb. 8, 2018

(65) Prior Publication Data

US 2018/0160990 A1 Jun. 14, 2018

Related U.S. Application Data

(63) Continuation-in-part of application No. 15/224,812, filed on Aug. 1, 2016.
(Continued)

(51) Int. Cl.
*A61B 5/05* (2006.01)
*A61B 6/12* (2006.01)
(Continued)

(52) U.S. Cl.
CPC .............. *A61B 6/12* (2013.01); *A61B 6/00* (2013.01); *A61B 6/463* (2013.01); *A61B 6/466* (2013.01);
(Continued)

(58) Field of Classification Search
None
See application file for complete search history.

(56) References Cited

U.S. PATENT DOCUMENTS 5,706,324 A 1/1998 Wiesent et al.
5,852,646 A 12/1998 Klotz et al.
(Continued)

FOREIGN PATENT DOCUMENTS

CN 101190149 A 6/2008
DE 19919907 A1 11/2000
(Continued)

OTHER PUBLICATIONS

Examination Report issued in corresponding Application No. AU 2018204631 dated May 24, 2019 (4 pages).
(Continued)

*Primary Examiner* — Joel F Brutus

(57) ABSTRACT

A system for constructing fluoroscopic-based three-dimensional volumetric data of a target area within a patient from two-dimensional fluoroscopic images including a structure of markers, a fluoroscopic imaging device configured to acquire a sequence of images of the target area and of the structure of markers, and a computing device. The computing device is configured to estimate a pose of the fluoroscopic imaging device for at least a plurality of images of the sequence of images based on detection of a possible and most probable projection of the structure of markers as a whole on each image of the plurality of images. The computing device is further configured to construct fluoroscopic-based three-dimensional volumetric data of the target area based on the estimated poses of the fluoroscopic imaging device.

20 Claims, 11 Drawing Sheets

Related U.S. Application Data

(60) Provisional application No. 62/201,750, filed on Aug. 6, 2015.

(51) Int. Cl.
*A61B 6/00* (2006.01)
*A61B 34/20* (2016.01)
*A61B 90/00* (2016.01)

(52) U.S. Cl.
CPC ............ *A61B 6/487* (2013.01); *A61B 6/5235* (2013.01); *A61B 34/20* (2016.02); *A61B 2034/2046* (2016.02); *A61B 2034/2051* (2016.02); *A61B 2034/2065* (2016.02); *A61B 2090/367* (2016.02); *A61B 2090/3762* (2016.02); *A61B 2090/3908* (2016.02); *A61B 2090/3966* (2016.02); *A61B 2090/3983* (2016.02)

(56) References Cited

U.S. PATENT DOCUMENTS

| | | | |
|---|---|---|---|
| 5,930,329 | A | 7/1999 | Navab |
| 5,951,475 | A | 9/1999 | Gueziec et al. |
| 5,963,612 | A | 10/1999 | Navab |
| 5,963,613 | A | 10/1999 | Navab |
| 6,038,282 | A | 3/2000 | Wiesent et al. |
| 6,049,582 | A | 4/2000 | Navab |
| 6,050,724 | A | 4/2000 | Schmitz et al. |
| 6,055,449 | A | 4/2000 | Navab |
| 6,081,577 | A | 6/2000 | Webber |
| 6,118,845 | A | 9/2000 | Simon et al. |
| 6,120,180 | A | 9/2000 | Graumann |
| 6,236,704 | B1 | 5/2001 | Navab et al. |
| 6,243,439 | B1 | 6/2001 | Arai et al. |
| 6,285,739 | B1 | 9/2001 | Rudin et al. |
| 6,289,235 | B1 | 9/2001 | Webber et al. |
| 6,317,621 | B1 | 11/2001 | Graumann et al. |
| 6,351,513 | B1 | 2/2002 | Bani-Hashemi et al. |
| 6,359,960 | B1 | 3/2002 | Wahl et al. |
| 6,382,835 | B2 | 5/2002 | Graumann et al. |
| 6,389,104 | B1 | 5/2002 | Bani-Hashemi et al. |
| 6,404,843 | B1 | 6/2002 | Vaillant |
| 6,424,731 | B1 | 7/2002 | Launay et al. |
| 6,484,049 | B1 | 11/2002 | Seeley et al. |
| 6,485,422 | B1 | 11/2002 | Mikus et al. |
| 6,490,475 | B1 | 12/2002 | Seeley et al. |
| 6,491,430 | B1 | 12/2002 | Seissler |
| 6,546,068 | B1 | 4/2003 | Shimura |
| 6,546,279 | B1 | 4/2003 | Bova et al. |
| 6,549,607 | B1 | 4/2003 | Webber |
| 6,585,412 | B2 | 7/2003 | Mitschke |
| 6,662,036 | B2 | 12/2003 | Cosman |
| 6,666,579 | B2 | 12/2003 | Jensen |
| 6,697,664 | B2 | 2/2004 | Kienzle, III et al. |
| 6,707,878 | B2 | 3/2004 | Claus et al. |
| 6,714,810 | B2 | 3/2004 | Grzeszczuk et al. |
| 6,731,283 | B1 | 5/2004 | Navab |
| 6,731,970 | B2 | 5/2004 | Schlossbauer et al. |
| 6,768,784 | B1 | 7/2004 | Green et al. |
| 6,782,287 | B2 | 8/2004 | Grzeszczuk et al. |
| 6,785,356 | B2 | 8/2004 | Grass et al. |
| 6,785,571 | B2 | 8/2004 | Glossop |
| 6,801,597 | B2 | 10/2004 | Webber |
| 6,810,278 | B2 | 10/2004 | Webber et al. |
| 6,823,207 | B1 | 11/2004 | Jensen et al. |
| 6,851,855 | B2 | 2/2005 | Mitschke et al. |
| 6,856,826 | B2 | 2/2005 | Seeley et al. |
| 6,856,827 | B2 | 2/2005 | Seeley et al. |
| 6,865,253 | B2 | 3/2005 | Blumhofer et al. |
| 6,898,263 | B2 | 5/2005 | Avinash et al. |
| 6,912,265 | B2 | 6/2005 | Hebecker et al. |
| 6,928,142 | B2 | 8/2005 | Shao et al. |
| 6,944,260 | B2 | 9/2005 | Hsieh et al. |
| 6,956,927 | B2 | 10/2005 | Sukeyasu et al. |
| 7,010,080 | B2 | 3/2006 | Mitschke et al. |
| 7,010,152 | B2 | 3/2006 | Bojer et al. |
| 7,035,371 | B2 | 4/2006 | Boese et al. |
| 7,048,440 | B2 | 5/2006 | Graumann et al. |
| 7,066,646 | B2 | 6/2006 | Pescatore et al. |
| 7,106,825 | B2 | 9/2006 | Gregerson et al. |
| 7,117,027 | B2 | 10/2006 | Zheng et al. |
| 7,129,946 | B2 | 10/2006 | Ditt et al. |
| 7,130,676 | B2 | 10/2006 | Barrick |
| 7,142,633 | B2 | 11/2006 | Eberhard et al. |
| 7,147,373 | B2 | 12/2006 | Cho et al. |
| 7,165,362 | B2 | 1/2007 | Jobs et al. |
| 7,186,023 | B2 | 3/2007 | Morita et al. |
| 7,251,522 | B2 | 7/2007 | Essenreiter et al. |
| 7,327,872 | B2 | 2/2008 | Vaillant et al. |
| 7,343,195 | B2 | 3/2008 | Strommer et al. |
| 7,369,641 | B2 | 5/2008 | Tsubaki et al. |
| 7,426,256 | B2 | 9/2008 | Rasche et al. |
| 7,440,538 | B2 | 10/2008 | Tsujii |
| 7,467,007 | B2 | 12/2008 | Lothert |
| 7,474,913 | B2 | 1/2009 | Durlak |
| 7,502,503 | B2 | 3/2009 | Bojer et al. |
| 7,505,549 | B2 | 3/2009 | Ohishi et al. |
| 7,508,388 | B2 | 3/2009 | Barruss et al. |
| 7,603,155 | B2 | 10/2009 | Jensen |
| 7,620,223 | B2 | 11/2009 | Xu et al. |
| 7,639,866 | B2 | 12/2009 | Pomero et al. |
| 7,664,542 | B2 | 2/2010 | Boese et al. |
| 7,671,887 | B2 | 3/2010 | Pescatore et al. |
| 7,689,019 | B2 | 3/2010 | Boese et al. |
| 7,689,042 | B2 | 3/2010 | Brunner et al. |
| 7,693,263 | B2 | 4/2010 | Bouvier et al. |
| 7,711,082 | B2 | 5/2010 | Fujimoto et al. |
| 7,711,083 | B2 | 5/2010 | Heigl et al. |
| 7,711,409 | B2 | 5/2010 | Keppel et al. |
| 7,712,961 | B2 | 5/2010 | Horndler et al. |
| 7,720,520 | B2 | 5/2010 | Willis |
| 7,725,165 | B2 | 5/2010 | Chen et al. |
| 7,734,329 | B2 | 6/2010 | Boese et al. |
| 7,742,557 | B2 | 6/2010 | Brunner et al. |
| 7,761,135 | B2 | 7/2010 | Pfister et al. |
| 7,778,685 | B2 | 8/2010 | Evron et al. |
| 7,778,690 | B2 | 8/2010 | Boese et al. |
| 7,787,932 | B2 | 8/2010 | Vilsmeier et al. |
| 7,804,991 | B2 | 9/2010 | Abovitz et al. |
| 7,831,096 | B2 | 11/2010 | Williamson, Jr. |
| 7,835,779 | B2 | 11/2010 | Anderson et al. |
| 7,844,094 | B2 | 11/2010 | Jeung et al. |
| 7,853,061 | B2 | 12/2010 | Gorges et al. |
| 7,877,132 | B2 | 1/2011 | Rongen et al. |
| 7,899,226 | B2 | 3/2011 | Pescatore et al. |
| 7,907,989 | B2 | 3/2011 | Borgert et al. |
| 7,912,180 | B2 | 3/2011 | Zou et al. |
| 7,912,262 | B2 | 3/2011 | Timmer et al. |
| 7,949,088 | B2 | 5/2011 | Nishide et al. |
| 7,950,849 | B2 | 5/2011 | Claus et al. |
| 7,991,450 | B2 | 8/2011 | Virtue et al. |
| 8,000,436 | B2 | 8/2011 | Seppi et al. |
| 8,043,003 | B2 | 10/2011 | Vogt et al. |
| 8,045,780 | B2 | 10/2011 | Boese et al. |
| 8,050,739 | B2 | 11/2011 | Eck et al. |
| 8,090,168 | B2 | 1/2012 | Washburn et al. |
| 8,104,958 | B2 | 1/2012 | Weiser et al. |
| 8,111,894 | B2 | 2/2012 | Van De Haar |
| 8,111,895 | B2 | 2/2012 | Spahn |
| 8,126,111 | B2 | 2/2012 | Uhde et al. |
| 8,126,241 | B2 | 2/2012 | Zarkh et al. |
| 8,150,131 | B2 | 4/2012 | Harer et al. |
| 8,180,132 | B2 | 5/2012 | Gorges et al. |
| 8,195,271 | B2 | 6/2012 | Rahn |
| 8,200,316 | B2 | 6/2012 | Keppel et al. |
| 8,208,708 | B2 | 6/2012 | Homan et al. |
| 8,229,061 | B2 | 7/2012 | Hanke et al. |
| 8,248,413 | B2 | 8/2012 | Gattani et al. |
| 8,270,691 | B2 | 9/2012 | Xu et al. |
| 8,271,068 | B2 | 9/2012 | Khamene et al. |
| 8,275,448 | B2 | 9/2012 | Camus et al. |
| 8,306,303 | B2 | 11/2012 | Bruder et al. |
| 8,311,617 | B2 | 11/2012 | Keppel et al. |

(56) References Cited

U.S. PATENT DOCUMENTS

| | | | |
|---|---|---|---|
| 8,320,992 B2 | 11/2012 | Frenkel et al. |
| 8,326,403 B2 | 12/2012 | Pescatore et al. |
| 8,340,379 B2 | 12/2012 | Razzaque et al. |
| 8,345,817 B2 | 1/2013 | Fuchs et al. |
| 8,374,416 B2 | 2/2013 | Gagesch et al. |
| 8,374,678 B2 | 2/2013 | Graumann |
| 8,423,117 B2 | 4/2013 | Pichon et al. |
| 8,442,618 B2 | 5/2013 | Strommer et al. |
| 8,515,527 B2 | 8/2013 | Vaillant et al. |
| 8,526,688 B2 | 9/2013 | Groszmann et al. |
| 8,526,700 B2 | 9/2013 | Isaacs |
| 8,532,258 B2 | 9/2013 | Bulitta et al. |
| 8,532,259 B2 | 9/2013 | Shedlock et al. |
| 8,548,567 B2 | 10/2013 | Maschke et al. |
| 8,625,869 B2 | 1/2014 | Harder et al. |
| 8,666,137 B2 | 3/2014 | Nielsen et al. |
| 8,670,603 B2 | 3/2014 | Tolkowsky et al. |
| 8,675,996 B2 | 3/2014 | Liao et al. |
| 8,693,622 B2 | 4/2014 | Graumann et al. |
| 8,693,756 B2 | 4/2014 | Tolkowsky et al. |
| 8,694,075 B2 | 4/2014 | Groszmann et al. |
| 8,706,186 B2 | 4/2014 | Fichtinger et al. |
| 8,712,129 B2 | 4/2014 | Strommer et al. |
| 8,718,346 B2 | 5/2014 | Isaacs et al. |
| 8,750,582 B2 | 6/2014 | Boese et al. |
| 8,755,587 B2 | 6/2014 | Bender et al. |
| 8,781,064 B2 | 7/2014 | Fuchs et al. |
| 8,792,704 B2 | 7/2014 | Isaacs |
| 8,798,339 B2 | 8/2014 | Mielekamp et al. |
| 8,831,310 B2 | 9/2014 | Razzaque et al. |
| 8,855,748 B2 | 10/2014 | Keppel et al. |
| 9,001,121 B2 | 4/2015 | Finlayson et al. |
| 9,001,962 B2 | 4/2015 | Funk |
| 9,008,367 B2 | 4/2015 | Tolkowsky et al. |
| 9,031,188 B2 | 5/2015 | Belcher et al. |
| 9,036,777 B2 | 5/2015 | Ohishi et al. |
| 9,042,624 B2 | 5/2015 | Dennerlein |
| 9,044,190 B2 | 6/2015 | Rubner et al. |
| 9,087,404 B2 | 7/2015 | Hansis et al. |
| 9,095,252 B2 | 8/2015 | Popovic |
| 9,104,902 B2 | 8/2015 | Xu et al. |
| 9,111,175 B2 | 8/2015 | Strommer et al. |
| 9,135,706 B2 | 9/2015 | Zagorchev et al. |
| 9,171,365 B2 | 10/2015 | Mareachen et al. |
| 9,179,878 B2 | 11/2015 | Jeon |
| 9,216,065 B2 | 12/2015 | Cohen et al. |
| 9,232,924 B2 | 1/2016 | Liu et al. |
| 9,262,830 B2 | 2/2016 | Bakker et al. |
| 9,265,468 B2 | 2/2016 | Rai et al. |
| 9,277,893 B2 | 3/2016 | Tsukagoshi et al. |
| 9,280,837 B2 | 3/2016 | Grass et al. |
| 9,282,944 B2 | 3/2016 | Fallavollita et al. |
| 9,401,047 B2 | 7/2016 | Bogoni et al. |
| 9,406,134 B2 | 8/2016 | Klingenbeck-Regn |
| 9,445,772 B2 | 9/2016 | Callaghan |
| 9,445,776 B2 | 9/2016 | Han et al. |
| 9,466,135 B2 | 10/2016 | Koehler et al. |
| 9,743,896 B2 | 8/2017 | Averbuch |
| 2002/0122536 A1 | 9/2002 | Kerrien et al. |
| 2002/0163996 A1 | 11/2002 | Kerrien et al. |
| 2002/0188194 A1 | 12/2002 | Cosman |
| 2003/0088179 A1 | 5/2003 | Seeley et al. |
| 2005/0220264 A1 | 10/2005 | Homegger |
| 2005/0245807 A1 | 11/2005 | Boese et al. |
| 2005/0281385 A1 | 12/2005 | Johnson et al. |
| 2006/0182216 A1 | 8/2006 | Lauritsch et al. |
| 2006/0251213 A1 | 11/2006 | Bernhardt et al. |
| 2007/0276216 A1 | 11/2007 | Beyar et al. |
| 2010/0284601 A1* | 11/2010 | Rubner ............... A61B 6/4405 382/132 |
| 2013/0172732 A1* | 7/2013 | Kiraly ................ A61B 6/5241 600/424 |
| 2013/0223702 A1* | 8/2013 | Holsing ............... A61B 5/061 382/128 |
| 2015/0086955 A1* | 3/2015 | Poniatowski ........ G09B 23/28 434/267 |
| 2015/0227679 A1 | 8/2015 | Kamer et al. |
| 2016/0005194 A1 | 1/2016 | Schretter et al. |
| 2016/0206380 A1 | 7/2016 | Sparks et al. |
| 2016/0287343 A1 | 10/2016 | Eichler et al. |

FOREIGN PATENT DOCUMENTS

| | | |
|---|---|---|
| DE | 69726415 T2 | 9/2004 |
| DE | 10 2004 004 620 A1 | 8/2005 |
| EP | 0917855 A1 | 5/1999 |
| EP | 1 593 343 A2 | 11/2005 |
| EP | 3127485 A1 | 2/2017 |
| JP | 11197259 | 7/1999 |
| WO | 99/44503 A1 | 9/1999 |
| WO | 01/87136 A2 | 11/2001 |
| WO | 2004081877 A1 | 9/2004 |
| WO | 2005015125 A1 | 2/2005 |
| WO | 2005/082246 A1 | 9/2005 |
| WO | 2008038283 A2 | 4/2008 |
| WO | 2009081297 A2 | 7/2009 |
| WO | 2014186715 A1 | 11/2014 |
| WO | 2015101948 A2 | 7/2015 |
| WO | 2019006258 A1 | 1/2019 |

OTHER PUBLICATIONS

Canadian Office Action issued in Appl. No. 2,937,825 dated Mar. 26, 2018 (4 pages).
Office Action issued in Chinese Appl. No. 201610635896.X dated Jul. 23, 2018, together with English language translation (16 pages).
Yingchao Li, et al., "Distortion Correction and Geometric Calibration for X-Ray Angiography System", IEEE Transactions on Nuclear Science, vol. 56, No. 3, (2009), pp. 608-619.
Extended European Search Report issued in corresponding Appl. No. EP 19156045.7 dated Jul. 15, 2019 (9 pages).
Examination Report issued in corresponding Appl. No. AU 2018204631 dated Aug. 12, 2019 (3 pages).
Extended European Search Report from Appl. No. EP 16182953.6-1666 dated Jan. 2, 2017.
CT scan—Wikipedia, the free encyclopedia [retrieved from internet on Mar. 30, 2017].<URL:http://web.archive.org/web/20150630170453/https://en.wikipedia.org/wiki/CT_scan > published on Jun. 30, 2015 as per Wayback Machine.
Australian Examination Report No. 2 issued in Appl. No. AU 2016210747 dated Oct. 18, 2017 (4 pages).
Australian Examination Report issued in corresponding Appl. No. AU 2019200594 dated Aug. 20, 2019 (5 pages).
Japanese Office Action issued in corresponding Appl. No. JP 2019-021423, together with English language translation, dated Jan. 8, 2020 (7 pages).

* cited by examiner

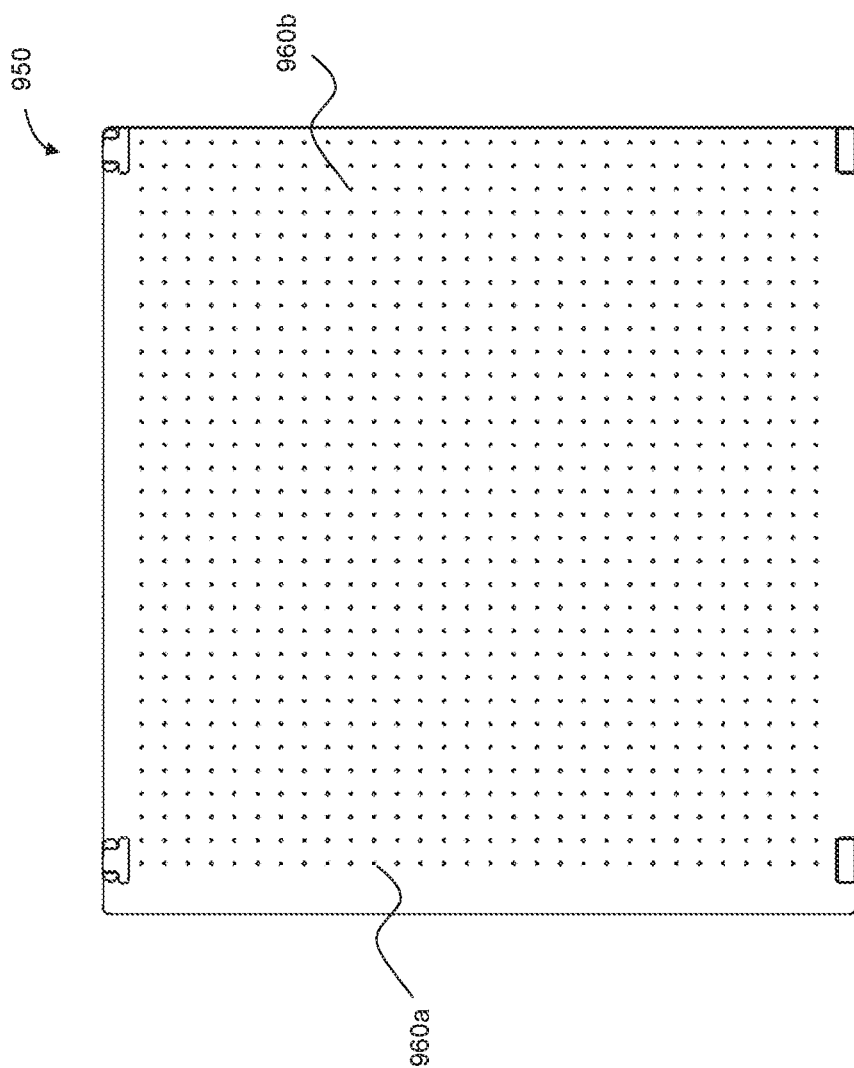

ized volumetric data may be used to confirm placement of a medical device during a medical procedure.

SYSTEM AND METHOD FOR LOCAL THREE DIMENSIONAL VOLUME RECONSTRUCTION USING A STANDARD FLUOROSCOPE

CROSS-REFERENCE TO RELATED APPLICATIONS

This application is a continuation-in-part of U.S. application Ser. No. 15/224,812, filed on Aug. 1, 2016 which claims priority to U.S. Provisional Application Ser. No. 62/201,750, filed on Aug. 6, 2015. The disclosure of each of the prior applications is considered part of and is incorporated by reference in the disclosure of this application.

BACKGROUND

Technical Field

The present disclosure relates to a system, apparatus, and method of navigation, position confirmation and position correction for surgical procedures. More particularly, the present disclosure relates to a system and method for constructing a fluoroscopic-based three-dimensional volume from two dimensional fluoroscopic images captured using a standard fluoroscopic imaging device and for utilizing this fluoroscopic-based three dimensional volume for real-time determination of the location of a medical device relative to a target within a patient.

Description of Related Art

There are several commonly applied medical methods, such as endoscopic procedures or minimally invasive procedures, for treating various maladies affecting organs including the liver, brain, heart, lung, gall bladder, kidney and bones. Often, one or more imaging modalities, such as magnetic resonance imaging, ultrasound imaging, computed tomography (CT), as well as others are employed by clinicians to identify areas of interest within a patient and ultimately targets for treatment.

For example, an endoscopic approach has proven useful in navigating to areas of interest within a patient, and particularly so for areas within luminal networks of the body such as the lungs. To enable the endoscopic, and more particularly the bronchoscopic, approach in the lungs, endobronchial navigation systems have been developed that use previously acquired MRI data or CT image data to generate a three dimensional rendering or volume of the particular body part such as the lungs. In particular, previously acquired images, acquired from an MRI scan or CT scan of the patient, are utilized to generate a three dimensional or volumetric rendering of the patient.

The resulting volume generated from the MRI scan or CT scan is then utilized to create a navigation plan to facilitate the advancement (e.g., manually or via a console, when robotic surgery is performed) of a navigation catheter (or other suitable device) through a bronchoscope and a branch of the bronchus of a patient to an area of interest. Electromagnetic tracking may be utilized in conjunction with the CT data to facilitate guidance of the navigation catheter through the branch of the bronchus to the area of interest. In certain instances, the navigation catheter may be positioned within one of the airways of the branched luminal networks adjacent to, or within, the area of interest to provide access for one or more medical instruments.

As another example, minimally invasive procedures, such as laparoscopy procedures, including robotic-assisted surgery, may employ intraoperative fluoroscopy in order to increase visualization, e.g., for guidance and lesion locating, or in order to prevents injury and complications.

In order to generate a navigation plan, or in order to even generate a three dimensional or volumetric rendering of the patient's anatomy, such as the lung, a clinician is required to utilize an MRI system or CT system to acquire the necessary image data for construction of the three dimensional volume. An MRI system or CT-based imaging system is extremely costly, and in many cases not available in the same location as the location where a navigation plan is generated or where a navigation procedure is carried out.

A fluoroscopic imaging device is commonly located in the operating room during navigation procedures. The standard fluoroscopic imaging device may be used by a clinician to visualize and confirm the placement of a tool or a medical device after it has been navigated to a desired location. However, although standard fluoroscopic images display highly dense objects such as metal tools and bones as well as large soft-tissue objects such as the heart, the fluoroscopic images have difficulty resolving small soft-tissue objects of interest such as lesions. Further, the fluoroscope image is only a two dimensional projection. In order to be able to see small soft-tissue objects in three dimensional space, an X-ray volumetric reconstruction is needed. Several solutions exist that provide three dimensional volume reconstruction of soft-tissues such as CT and Cone-beam CT which are extensively used in the medical world. These machines algorithmically combine multiple X-ray projections from known, calibrated X-ray source positions into three dimensional volume in which the soft-tissues are visible.

In order to navigate tools to a remote soft-tissue target for biopsy or treatment, both the tool and the target should be visible in some sort of a three dimensional guidance system. The majority of these systems use some X-ray device to see through the body. For example, a CT machine can be used with iterative scans during procedure to provide guidance through the body until the tools reach the target. This is a tedious procedure as it requires several full CT scans, a dedicated CT room and blind navigation between scans. In addition, each scan requires the staff to leave the room. Another option is a Cone-beam CT machine which is available in some operation rooms and is somewhat easier to operate, but is expensive and like the CT only provides blind navigation between scans, requires multiple iterations for navigation and requires the staff to leave the room.

Accordingly, there is a need for a system that can achieve the benefits of the CT and Cone-beam CT three dimensional image guidance without the underlying costs, preparation requirements, and radiation side effects associated with these systems. Furthermore, there is a need for a system and a method which facilitate relatively accurate navigation of medical devices in relation to a target and in particular to facilitate an effective treatment of the target.

SUMMARY

The present disclosure is directed to a system and method for constructing three dimensional volumetric data in which small soft-tissue objects are visible from a video stream (or plurality of images) captured by a standard fluoroscopic imaging device available in most procedure rooms. The fluoroscopic-based constructed three dimensional volumetric data may be used for guidance, navigation planning, improved navigation accuracy, navigation confirmation, and treatment confirmation.

Soft tissue objects are not visible in standard fluoroscopic images and video because they are obscured by dense objects such as dense tissue. The present disclosure is directed to a system and method for creating a three-dimensional pseudo-volume in which the obscuring objects are filtered based on the three dimensional position, and then projected back into two dimensions. In one aspect, multiple fluoroscopic images, each captured at a different angle, are utilized to construct the three dimensional pseudo-volume data. The present disclosure describes a system and method which is capable of constructing the three dimensional pseudo-volume data utilizing fluoroscopic images captured from a short range of angles relative to a patient or target region of a patient. Additionally, the present disclosure is also directed to a system and method for improving a previously created three dimensional rendering utilizing two dimensional images, or video, captured by a standard fluoroscopic imaging device.

As described in greater detail below, one aspect of the present disclosure is to determine three dimensional positions of features in the fluoroscopic video, such as three dimensional catheter position, three dimensional target tissue (for example a lesion) position, etc. In order to accomplish this, the pose of the fluoroscopic imaging device for each frame must be determined or known. If an external angle measurement device coupled to the fluoroscopic imaging device is utilized, then the angles and pose of the imaging device is known for each frame. However, when external measurement devices are not utilized other techniques are employed to determine the poses of the fluoroscopic imaging device for each frame, as described in greater detail below. For example, previously acquired CT scan data may be registered to the fluoroscopic video in order to algorithmically find the pose of the fluoroscope for each frame of the captured video. Alternatively, by tracking a few visible markers (two dimensional visible features) in the fluoroscopic video, the pose and three dimensional positions may be solved together by using some structure from motion technique. In some aspects, a structure of markers placed externally to the patient may be utilized. The poses of the fluoroscope may be then estimated based on detection of a possible and most probable projection of the structure of markers as a whole on each image of the plurality of images In some aspects, easier techniques in which the poses are known (by an angle measurement device) may be utilized and only the three dimensional features' positions need to be solved. In order to correct for movements, at least one marker (or a surgical device such as a catheter tip) may be utilized.

Multiple fluoroscope two dimensional images can be processed algorithmically to create pseudo three dimensional volumetric data, similar to Cone-beam CT, but with varying arbitrary angle range and fluoroscope poses, where the fluoroscope is rotated manually. The angle range may be very small (~30°) which may result in poor three dimensional reconstruction quality. The algorithm used is an iterative accelerated projection/back-projection method which unlike the analytic algorithms (e.g., Radon transform, FDK) doesn't assume any predetermined angle range or angle rotation rate. In order to overcome the poor three dimensional reconstruction, instead of displaying the raw three dimensional reconstructed data to the user, the three dimensional reconstruction may be cropped around the area of interest (also referred to herein as the "FluoroCT Blob").

The cropped three dimensional data may be then reprojected into two dimensional virtual fluoroscope images in which local soft-tissue features are visible, in particular. The reprojected two dimensional images are of good quality (compared to the poor three dimensional reconstruction), especially if the projections are done from the same fluoroscope poses as were seen in the video.

In order to reconstruct the three dimensional data, the pose of the fluoroscopic imaging device must be determined for each two dimensional fluoroscope frame in the video, relative to some fixed coordinate system. The pose of the fluoroscopic imaging device for each frame captured may be determined using any of the methods described below. For example the pose may be determined using an external measurement device coupled to the fluoroscopic imaging device or by utilizing a structure of markers places externally to the patient and with respect to the target.

Additionally, or alternatively, the pose may be determined using an external measurement device and a single marker or a catheter tip. Specifically, in some cases, the fluoroscope (or C-arm) may jitter during rotation, in which case some stabilization is needed. Unfortunately, due to filtering, the angle measurement device may still report smooth angles throughout the video, ignoring the high-frequencies which are present in the actual camera poses. In this case, a single two dimensional marker can be tracked throughout the video and used to stabilize the camera poses, or to increase their accuracy at the area of the marker. Since the marker will usually be located at the region of interest, this increases the camera pose accuracy in this region, and thus improves the three dimensional reconstruction quality. This method can also be used to compensate for patient body movement such as breathing during the video. Instead of using the camera pose as reported by the angle measurement device, a compensated camera pose is computed using the tracked two dimensional marker, such that all camera poses will be correct relative to it. The single marker used can be the tip of a tool or a catheter which is currently inserted to the patient.

Additionally, or alternatively, the pose may be determined via registration of the fluoroscopic video to previously acquired CT data. Specifically, a previously acquired CT of the patient may be available. In this case, each frame of the fluoroscope video can be registered to a virtual fluoroscopic frame of the CT (camera pose is searched in CT space until the virtual fluoroscopic image, corresponding to the camera pose, matches the one seen in the video). In this way, the camera pose is realized using image-based features matching.

Additionally, or alternatively, the pose may be determined via a structure of markers. Specifically, the structure of markers is positioned externally to the patient, e.g., under the patient, while capturing the images. The structure of markers is further positioned such that each image includes a projection of at least a portion of the structure. A probability map may be then generated for each image indicating the probability of each pixel in the image to be a marker of the structure of markers. Multiple virtual candidate for the projection of the structure of markers on the image may be generated by virtually positioning the fluoroscope in possible different locations, including possible orientations. The candidate having the highest probability of being the projection of the structure of markers on the image may be then identified based on the probability map. The virtual pose of the fluoroscope associated with the identified candidate may be then determined as the estimated pose of the fluoroscope while capturing the image. Optionally, the process of identifying a candidate may be refined. A locally deformed version of the candidate may be generated based on the probability map in order to maximize its probability of being the projection of the structure of markers on the image. A new virtual candidate may be then fitted to the locally deformed version of the identified candidate. The virtual pose of the fluoroscope which would generate the new improved candidate is the calculated and determined as the estimated pose of the fluoroscope while capturing the image.

Additionally, or alternatively, the camera pose may be determined using structure from motion techniques. Specifically, if numerous two dimensional features can be tracked throughout the two dimensional video frames, from beginning to end, then these two dimensional features can be used to realize camera poses (together with three dimensional feature positions) for each frame. These features can be artificial markers which were introduced to the patient during procedure.

Filtering the obscuring tissue from the tissue of interest can be done by cropping at a distance from the center of the generated three dimensional pseudo-volume data, cropping at a distance from the tool/catheter, or registering to previously obtained three dimensional volume data (CT) and using it to know which objects to filter.

Once the soft-tissue (such as a target lesion) is visible in the three dimensional reconstructed data (or in the two dimensional enhanced FluoroCT images), all three dimensional information in fluoroscope coordinates can be obtained. When working with the raw three dimensional reconstructed data the three dimensional information is obtained directly from the data. Alternatively, when working with the two dimensional enhanced FluoroCT images, 2-angles markings are needed in order to realize three dimensional positions (triangulation). In some embodiments, the three-dimensional reconstructed data is divided into slices, which are thin enough such that triangulation is not required in order to obtain three-dimensional position data.

The obtained three dimensional data may be utilized for real-time determination or confirmation of tool to soft-tissue target three dimensional relation. For example, the data may be used to determine whether the tool reached the target, the orientation of the tool relative to the target, the distance between the tool and the target, or whether the target falls within an ablation zone of the tool.

Additionally, or alternatively, the three dimensional data may be utilized for correction of navigation. For example, the three dimensional positions can be transformed from fluoroscope coordinates into navigation system coordinates to improve navigation system accuracy at the region of interest. In one aspect, when utilized in an EMN system, fluoroscope coordinates can be transformed to antenna coordinates by assuming that the C-arm is perfectly perpendicular to the antenna and matching the catheter tip, seen in the fluoroscope video, to the catheter position in antenna at the time the video was taken. Fluoroscopic to/from antenna registration can also be achieved by computing the angle between the C-arm and the antenna using the Earth's magnetic field, attaching an EMN sensor to the fluoroscopic imaging device, or aligning a known two dimensional feature of the antenna.

Aspects of the present disclosure are described in detail with reference to the figures wherein like reference numerals identify similar or identical elements. As used herein, the term "distal" refers to the portion that is being described which is further from a user, while the term "proximal" refers to the portion that is being described which is closer to a user.

According to one aspect of the present disclosure, a system for constructing fluoroscopic-based three dimensional volumetric data from two dimensional fluoroscopic images is provided. The system includes a computing device configured to facilitate navigation of a medical device to a target area within a patient and a fluoroscopic imaging device configured to acquire a fluoroscopic video of the target area about a plurality of angles relative to the target area. The computing device is configured to determine a pose of the fluoroscopic imaging device for each frame of the fluoroscopic video and to construct fluoroscopic-based three-dimensional volumetric data of the target area in which soft tissue objects are visible, in particular, using a fast iterative three-dimensional construction algorithm. In aspects, the system is configured to determine the pose of the fluoroscopic imaging device by knowing the angle range of movement of the device and computing the relative rotational speed of the device along the range. In some aspects, the computing device is configured to determine a pose of the fluoroscopic imaging device for at least a plurality of frames of the fluoroscopic video via a structure of at least partially radio-opaque markers. In some aspects, the computing device is configured to construct fluoroscopic-based three dimensional volumetric data of the target area using a three dimensional construction algorithm, as known in the art.

The medical device or tool may be a catheter assembly including an extended working channel configured to be positioned within a luminal network of the patient or the medical device may be a radio-opaque marker configured to be placed within the target area. The radio-opaque marker is at least partially visible in the fluoroscopic video acquired. The medical device may be a surgical instrument used in a minimally invasive surgery, including robotic minimally invasive surgery.

The computing device may be further configured to create virtual fluoroscopic images of the patient from previously acquired CT volumetric data and register the generated virtual fluoroscopic images with the acquired fluoroscopic video. The pose of the fluoroscopic imaging device for each frame of the fluoroscopic video may be determined based on the registration between the fluoroscopic video and the virtual fluoroscopic images.

The computing device may further be configured to detect frames missing from the fluoroscopic video and supplement the detected missing frames with corresponding virtual fluoroscopic images. The fluoroscopic-based three dimensional volumetric data may be constructed based on the fluoroscopic video and the corresponding virtual fluoroscopic images. In one aspect, the fluoroscopic-based three dimensional volumetric data may be registered with previously acquired CT data using image-based techniques such as "mutual information." The fluoroscopic-based three dimensional volumetric data may be registered globally to the previously acquired CT data or locally, at the proximity of the target area of interest. A deep-learning based approach may be utilized in which the computing device "sees" many examples of suitable and non-suitable registrations and learns how to register the very two different modalities.

Additionally, the computing device may be further configured to track the two dimensional position or orientation of the medical device navigated to the target region throughout the fluoroscopic video. The computing device may be further configured to reconstruct positions of the medical device throughout the fluoroscopic video using a structure-from-motion technique. The pose of the fluoroscopic imaging device for each frame of the fluoroscopic video may be determined based on the reconstructed positions. Additionally, or alternatively, the pose of the fluoroscopic imaging device for each frame of the fluoroscopic video may be determined based on an external angle measuring device. The external angle measuring device may include an accelerometer, a gyroscope, or a magnetic field sensor coupled to the fluoroscopic imaging device. Additionally, or alternatively, the pose of the fluoroscopic imaging device for each frame of the fluoroscopic video may be determined via a structure of markers positioned externally to the patient while capturing the images. Additionally, in aspects, the computing device may be configured to synchronize the captured frames of the target area and compensate for shifts in the fluoroscopic imaging device or patient movement to correct construction of the fluoroscopic-based three dimensional volumetric data. Additionally, or alternatively, the computing device may be configured to crop a region of interest from the fluoroscopic-based three dimensional volumetric data, project the cropped region of interest onto the captured frames, and sharpen or intensify at least one of the region of interest or the captured frame to identify soft tissue objects, or any other objects of interest.

In yet another aspect of the present disclosure a method for constructing fluoroscopic-based three dimensional volumetric data from two dimensional fluoroscopic images is provided. The method includes navigating a medical device to a target area within a patient, acquiring a fluoroscopic video of the target area about a plurality of angles relative to the target area using a fluoroscopic imaging device, determining a pose of the fluoroscopic imaging device for each frame of the fluoroscopic video, and constructing fluoroscopic-based three dimensional volumetric data of the target area in which soft tissue objects are visible using a fast iterative three dimensional construction algorithm. The medical device may be a catheter assembly including an extended working channel configured to be positioned within a luminal network of the patient or the medical device may be a radio-opaque marker configured to be placed within the target area. The radio-opaque marker is at least partially visible in the fluoroscopic video acquired.

The method may further include creating virtual fluoroscopic images of the patient from previously acquired CT volumetric data, and registering the fluoroscopic video with the virtual fluoroscopic images, wherein determining the pose of the fluoroscopic imaging device for each frame of the fluoroscopic video is based on the registration between the fluoroscopic video and the virtual fluoroscopic images. The method may further include detecting frames missing from the fluoroscopic video and supplementing the detected missing frames with corresponding virtual fluoroscopic images. Additionally, in aspects of the disclosure, the method may further include tracking the two dimensional position or orientation of the medical device navigated to the target region throughout the fluoroscopic video.

The positions of the medical device throughout the fluoroscopic video may be reconstructed using a structure-from-motion technique. The pose of the fluoroscopic imaging device for each frame of the fluoroscopic video may be determined based on the reconstructed positions. Additionally, or alternatively, the pose of the fluoroscopic imaging device for each frame of the fluoroscopic video may be determined based on an external angle measuring device. The external angle measuring device may include an accelerometer, a gyroscope, or a magnetic field sensor coupled to the fluoroscopic imaging device. Additionally, or alternatively, the pose of the fluoroscopic imaging device for each frame of the fluoroscopic video may be determined via a structure of at least partially radio-opaque markers positioned with respect to the target area, externally to the patient's body, while capturing the fluoroscopic images. Additionally, in aspects, the method may include synchronizing the captured frames of the target area and compensating for shifts in the fluoroscopic imaging device or patient movement to correct construction of the fluoroscopic-based three dimensional volumetric data. Additionally, or alternatively, the method may include cropping a region of interest from the fluoroscopic-based three dimensional volumetric data, projecting the cropped region of interest onto the captured frames, and sharpening or intensifying at least one of the region of interest or the captured frame to identify soft tissue objects.

BRIEF DESCRIPTION OF THE DRAWINGS

Various aspects and embodiments of the present disclosure are described hereinbelow with references to the drawings, wherein:

FIG. 9B is a schematic illustration of a two-dimensional grid structure of sphere markers in accordance with the method of FIG. 9A.

DETAILED DESCRIPTION

The present disclosure is directed to a system and method for constructing local three dimensional volumetric data, in which small soft-tissue objects are visible, from a video stream captured by a standard fluoroscopic imaging device available in most procedure rooms. The present disclosure is further directed to a system and method for determining a location of a medical device relative to a soft tissue target within a patient according to the three dimensional volumetric data. The constructed fluoroscopic-based local three dimensional volumetric data or the location of the medical device relative to the soft tissue target may be used for guidance, navigation planning, improved navigation accuracy, navigation confirmation, and treatment confirmation.

The terms "tool", "surgery instrument", "surgical device", "energy device", "medical device" and alike may be used hereby interchangeably.

Figure 1:
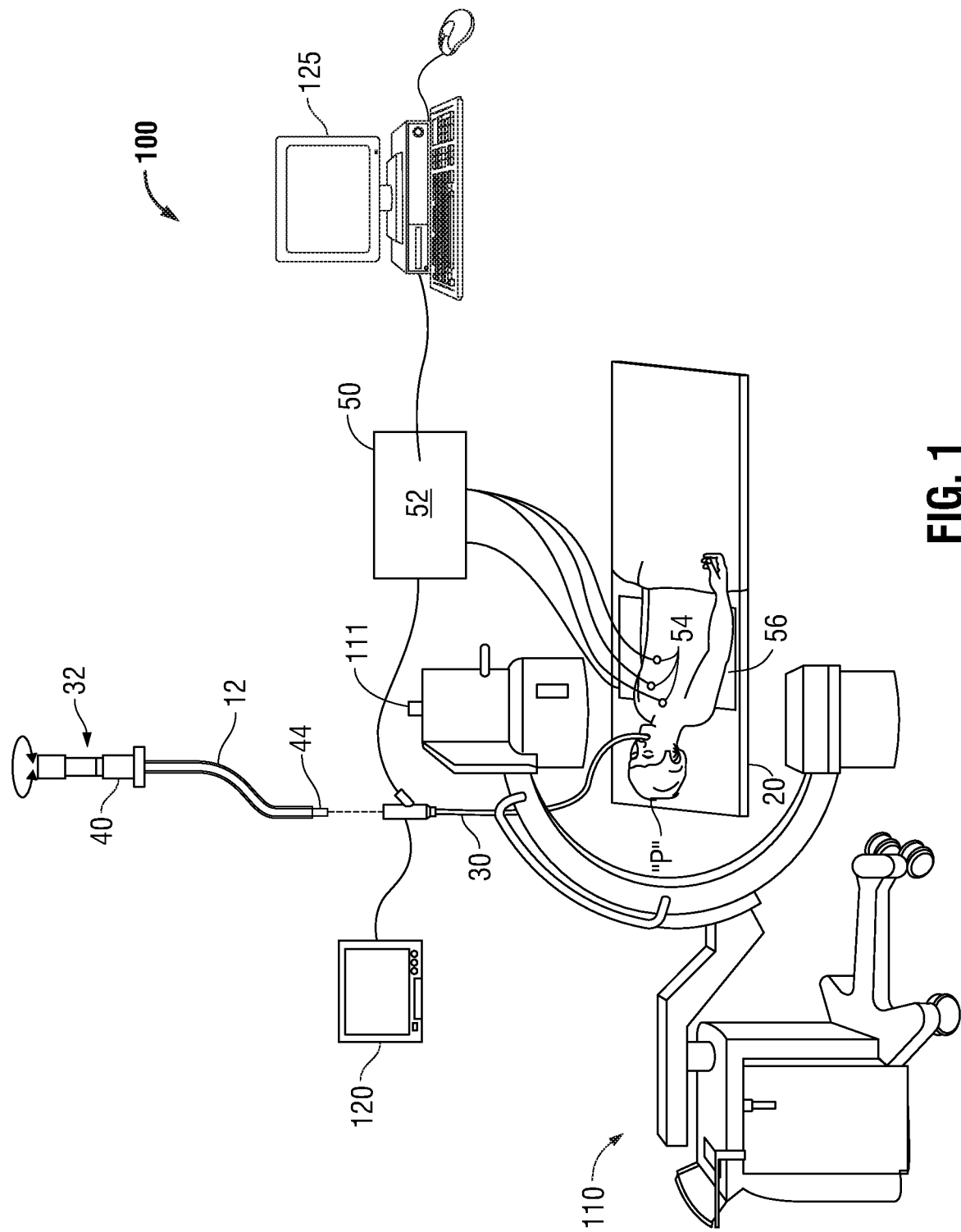
FIG. 1 is a perspective view of one illustrative embodiment of an electromagnetic navigation (EMN) system incorporating a fluoroscopic imaging device in accordance with the present disclosure.

FIG. 1 depicts an Electromagnetic Navigation (EMN) system 100 configured for reviewing CT image data to identify one or more targets, planning a pathway to an identified target (planning phase), navigating an extended working channel (EWC) 12 of a catheter assembly to a target (navigation phase) via a user interface, and confirming placement of the EWC 12 relative to the target. One such EMN system is the ELECTROMAGNETIC NAVIGATION BRONCHOSCOPY® system currently sold by Medtronic PLC. The target may be tissue of interest identified by review of the CT image data during the planning phase. Following navigation, a medical instrument, such as a biopsy tool or other tool, may be inserted into the EWC 12 to obtain a tissue sample from the tissue located at, or proximate to, the target.

As shown in FIG. 1, EWC 12 is part of a catheter guide assembly 40. In practice, the EWC 12 is inserted into bronchoscope 30 for access to a luminal network of the patient "P." Specifically, EWC 12 of catheter guide assembly 40 may be inserted into a working channel of bronchoscope 30 for navigation through a patient's luminal network. A locatable guide (LG) 32, including a sensor 44 is inserted into the EWC 12 and locked into position such that the sensor 44 extends a desired distance beyond the distal tip of the EWC 12. The position and orientation of the sensor 44 relative to the reference coordinate system, and thus the distal portion of the EWC 12, within an electromagnetic field can be derived. Catheter guide assemblies 40 are currently marketed and sold by Medtronic PLC under the brand names SUPERDIMENSION® Procedure Kits, or EDGE™ Procedure Kits, and are contemplated as useable with the present disclosure. For a more detailed description of the catheter guide assemblies 40, reference is made to commonly-owned U.S. Patent Publication No. 2014/0046315, filed on Mar. 15, 2013, by Ladtkow et al, U.S. Pat. Nos. 7,233,820, and 9,044,254, the entire contents of each of which are hereby incorporated by reference.

EMN system 100 generally includes an operating table 20 configured to support a patient "P," a bronchoscope 30 configured for insertion through the patient's "P's" mouth into the patient's "P's" airways; monitoring equipment 120 coupled to bronchoscope 30 (e.g., a video display, for displaying the video images received from the video imaging system of bronchoscope 30); a tracking system 50 including a tracking module 52, a plurality of reference sensors 54 and a transmitter mat 56; and a computing device 125 including software and/or hardware used to facilitate identification of a target, pathway planning to the target, navigation of a medical instrument to the target, and confirmation of placement of an EWC 12, or a suitable device therethrough, relative to the target.

A fluoroscopic imaging device 110 capable of acquiring fluoroscopic or x-ray images or video of the patient "P" is also included in this particular aspect of system 100. The images, series of images, or video captured by the fluoroscopic imaging device 110 may be stored within the fluoroscopic imaging device 110 or transmitted to computing device 125 for storage, processing, and display. Additionally, the fluoroscopic imaging device 110 may move relative to the patient "P" so that images may be acquired from different angles or perspectives relative to the patient "P" to create a fluoroscopic video. In one aspect of the present disclosure, fluoroscopic imaging device 110 includes an angle measurement device 111 which is configured to measure the angle of the fluoroscopic imaging device 110 relative to the patient "P." Angle measurement device 111 may be an accelerometer. Fluoroscopic imaging device 110 may include a single imaging device or more than one imaging device. In embodiments including multiple imaging devices, each imaging device may be a different type of imaging device or the same type. Further details regarding the imaging device 110 are described in U.S. Pat. No. 8,565,858, which is incorporated by reference in its entirety herein.

Computing device 125 may be any suitable computing device including a processor and storage medium, wherein the processor is capable of executing instructions stored on the storage medium. The computing device 125 may further include a database configured to store patient data, CT data sets including CT images, fluoroscopic data sets including fluoroscopic images and video, navigation plans, and any other such data. Although not explicitly illustrated, the computing device 125 may include inputs, or may otherwise be configured to receive, CT data sets, fluoroscopic images/video and other data described herein. Additionally, computing device 125 includes a display configured to display graphical user interfaces. Computing device 125 may be connected to one or more networks through which one or more databases may be accessed.

With respect to the planning phase, computing device 125 utilizes previously acquired CT image data for generating and viewing a three dimensional model of the patient's "P's" airways, enables the identification of a target on the three dimensional model (automatically, semi-automatically, or manually), and allows for determining a pathway through the patient's "P's" airways to tissue located at and around the target. More specifically, CT images acquired from previous CT scans are processed and assembled into a three dimensional CT volume, which is then utilized to generate a three dimensional model of the patient's "P's" airways. The three dimensional model may be displayed on a display associated with computing device 125, or in any other suitable fashion. Using computing device 125, various views of the three dimensional model or enhanced two dimensional images generated from the three dimensional model are presented. The enhanced two dimensional images may possess some three dimensional capabilities because they are generated from three dimensional data. The three dimensional model may be manipulated to facilitate identification of target on the three dimensional model or two dimensional images, and selection of a suitable pathway through the patient's "P's" airways to access tissue located at the target can be made. Once selected, the pathway plan, three dimensional model, and images derived therefrom, can be saved and exported to a navigation system for use during the navigation phase(s). One such planning software is the ILOGIC® planning suite currently sold by Medtronic PLC.

With respect to the navigation phase, a six degrees-of-freedom electromagnetic tracking system 50, e.g., similar to those disclosed in U.S. Pat. Nos. 8,467,589, 6,188,355, and published PCT Application Nos. WO 00/10456 and WO 01/67035, the entire contents of each of which are incorporated herein by reference, or other suitable positioning measuring system, is utilized for performing registration of the images and the pathway for navigation, although other configurations are also contemplated. Tracking system 50 includes a tracking module 52, a plurality of reference sensors 54, and a transmitter mat 56. Tracking system 50 is configured for use with a locatable guide 32 and particularly sensor 44. As described above, locatable guide 32 and sensor 44 are configured for insertion through an EWC 12 into a patient's "P's" airways (either with or without bronchoscope 30) and are selectively lockable relative to one another via a locking mechanism.

Transmitter mat 56 is positioned beneath patient "P." Transmitter mat 56 generates an electromagnetic field around at least a portion of the patient "P" within which the position of a plurality of reference sensors 54 and the sensor element 44 can be determined with use of a tracking module 52. One or more of reference sensors 54 are attached to the chest of the patient "P." The six degrees of freedom coordinates of reference sensors 54 are sent to computing device 125 (which includes the appropriate software) where they are used to calculate a patient coordinate frame of reference. Registration, as detailed below, is generally performed to coordinate locations of the three dimensional model and two dimensional images from the planning phase with the patient's "P's" airways as observed through the bronchoscope 30, and allow for the navigation phase to be undertaken with precise knowledge of the location of the sensor 44, even in portions of the airway where the bronchoscope 30 cannot reach. Further details of such a registration technique and their implementation in luminal navigation can be found in U.S. Patent Application Pub. No. 2011/0085720, the entire content of which is incorporated herein by reference, although other suitable techniques are also contemplated.

Registration of the patient's "P's" location on the transmitter mat 56 is performed by moving LG 32 through the airways of the patient's "P." More specifically, data pertaining to locations of sensor 44, while locatable guide 32 is moving through the airways, is recorded using transmitter mat 56, reference sensors 54, and tracking module 52. A shape resulting from this location data is compared to an interior geometry of passages of the three dimensional model generated in the planning phase, and a location correlation between the shape and the three dimensional model based on the comparison is determined, e.g., utilizing the software on computing device 125. In addition, the software identifies non-tissue space (e.g., air filled cavities) in the three dimensional model. The software aligns, or registers, an image representing a location of sensor 44 with a the three dimensional model and two dimensional images generated from the three dimension model, which are based on the recorded location data and an assumption that locatable guide 32 remains located in non-tissue space in the patient's "P's" airways. Alternatively, a manual registration technique may be employed by navigating the bronchoscope 30 with the sensor 44 to pre-specified locations in the lungs of the patient "P", and manually correlating the images from the bronchoscope to the model data of the three dimensional model.

Following registration of the patient "P" to the image data and pathway plan, a user interface is displayed in the navigation software which sets for the pathway that the clinician is to follow to reach the target. One such navigation software is the ILOGIC® navigation suite currently sold by Medtronic PLC.

Once EWC 12 has been successfully navigated proximate the target as depicted on the user interface, the locatable guide 32 may be unlocked from EWC 12 and removed, leaving EWC 12 in place as a guide channel for guiding medical instruments including without limitation, optical systems, ultrasound probes, marker placement tools, biopsy tools, ablation tools (i.e., microwave ablation devices), laser probes, cryogenic probes, sensor probes, and aspirating needles to the target.

Having described the components of system 100 depicted in FIG. 1, the following description of FIGS. 2-10 provides an exemplary workflow of using the components of system 100, including the fluoroscopic imaging device 110, to construct local three dimensional volumetric data of a desired region of interest and to determine medical device to soft-tissue target relation using the fluoroscopic imaging device 110 of system 100. The systems and methods described herein may be useful for visualizing a particular target region of a patient, and furthermore, for visualizing medical devices relative to the target during a medical procedure, utilizing imaging devices which are commonly located within a surgical setting during EMN procedures, thereby obviating the need for subsequent MRI or CT scans.

Figure 2:
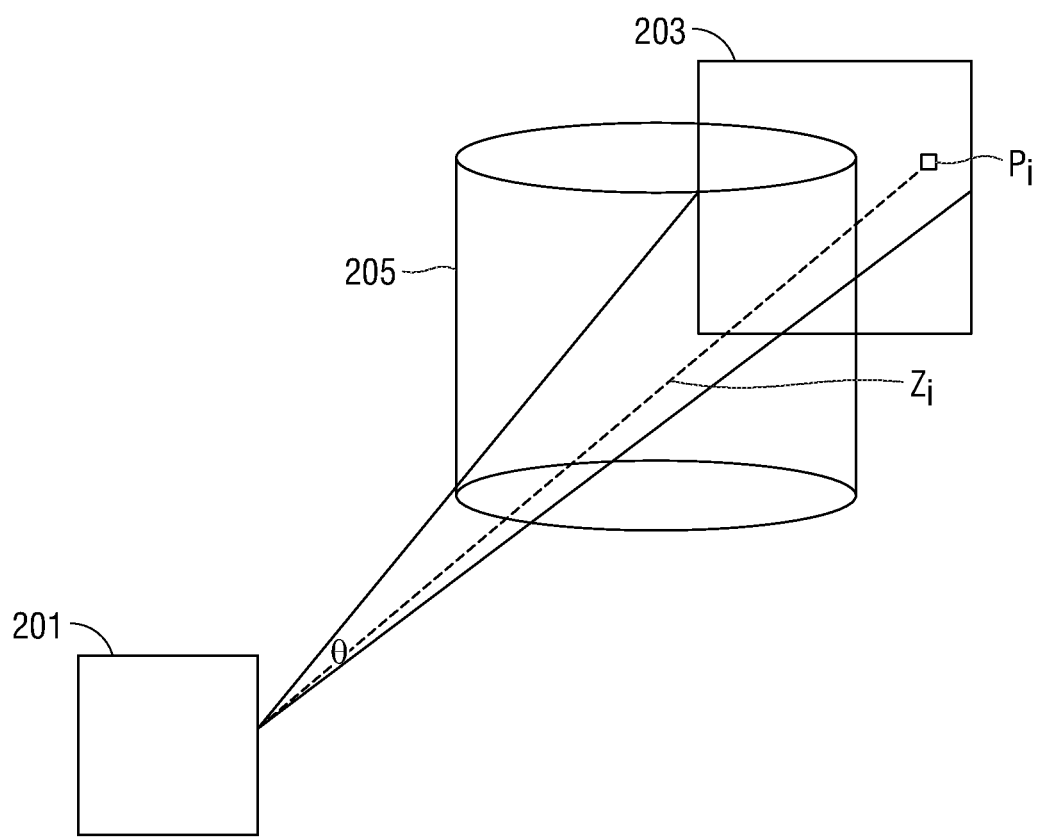
FIG. 2 illustrates a fluoroscopic imaging device model.

Turning now to FIG. 2, a fluoroscopic imaging device 110 model is illustrated. The fluoroscopic imaging device 110 includes an X-ray source 201 and a detector 203. The detector 203 defines a plurality of two dimensional pixels p. Each two dimensional pixel $P_i$ is associated with a single X-ray beam $l_i$, traversing three dimensional space from the X-ray source 201 to the detector 203. The detector 203 size D and the source-detector distance SDD determine the Field-of-View angle using the following formula:

$$\theta = 2\tan^{-1}\left(\frac{D}{2SDD}\right).$$

Different fluoroscopes differ primarily by detector size and source-detector distance. In the fluoroscopic data, pixels are not normalized to a specific scale. Their brightness depends on the gain/exposure used by the fluoroscope and on other objects in the scene which the X-rays traverse between the source and the detector such as the table, the surgical device, etc. In the CT data, each voxel is measured in Hounsfield units. Hounsfield units are measured with respect to the brightness observed of water and air using the following formula:

$$HU = 1000 \frac{\mu - \mu_{water}}{\mu_{water} - \mu_{air}}.$$

μ are attenuation coefficients. They range from 0 to infinity and measure how difficult it is for an X-ray beam $l_i$ to traverse through matter of the three dimensional volume 205. "Thicker" matter has a larger μ. HU scales attenuation coefficients such that air is placed at −1000, water at 0 and thicker matter goes up to infinity.

Using the Beer-Lambert law, each two dimensional pixel $p_i$ in the fluoroscope's detector 203 is given by:

$$p_{i,j} = I_0 \exp(-\int_{l_{i,j}} \mu(l) dl).$$

μ(x, y, z) is the attenuation coefficient of the three dimensional volume 205 at position (x, y, z). $I_0$ is the X-ray source 201 energy (higher energy produces brighter image). For simplicity, assume $I_0=1$. Taking the logarithm, each two dimensional pixel $p_i$ is represented by:

$$\log(p_{i,j}) = -\int_{l_{i,j}} \mu(l)\,dl.$$

This is true for each two dimensional detector pixel $p_i$ which provides a linear equation on the three dimensional attenuation coefficients. If many such equations are utilized (to solve for each two dimensional pixel $p_i$ of the detector 203) then the attenuation coefficients may be solved and the three dimensional volume data of the three dimensional volume 205 can be constructed.

Fluoroscope to CT—Discretization:

The three dimensional volume 205 can be divided into a discrete grid, with voxels sitting at $(x_k, y_k, z_k)$. Thus, the equation for solving each two dimensional pixel $p_i$ can then be written as:

$$\log(p_{i,j}) = -\Sigma_k w_k^{i,j} \mu(x_k, y_k, z_k).$$

The left hand side of the equation above is the observed two dimensional pixel $p_i$ of the detector 203 and the right hand side of the equation above is a weighted sum of the attenuation coefficients (that is to be solved) with $w_k^{i,j}$ which are determined by the known fluoroscopic imaging device position of the X-ray source 201.

In order to be able to solve for the volumetric attenuation coefficient values enough linear equations are needed, that is, enough two dimensional observations of different two dimensional pixels p are required. Standard detectors usually have 1024×1024 pixels, where each pixel is represented by a single equation. Therefore, many two dimensional observations are required to be solved for (many two dimensional observed pixels) to reconstruct a three dimensional volume (to solve for many voxels). That is many two dimensional pixels are required to solve for the many voxels. In order for the weights in the equations to be known, the fluoroscopic imaging device X-ray source 201 configuration (position, orientation, field of view) must be known.

Figure 9A:
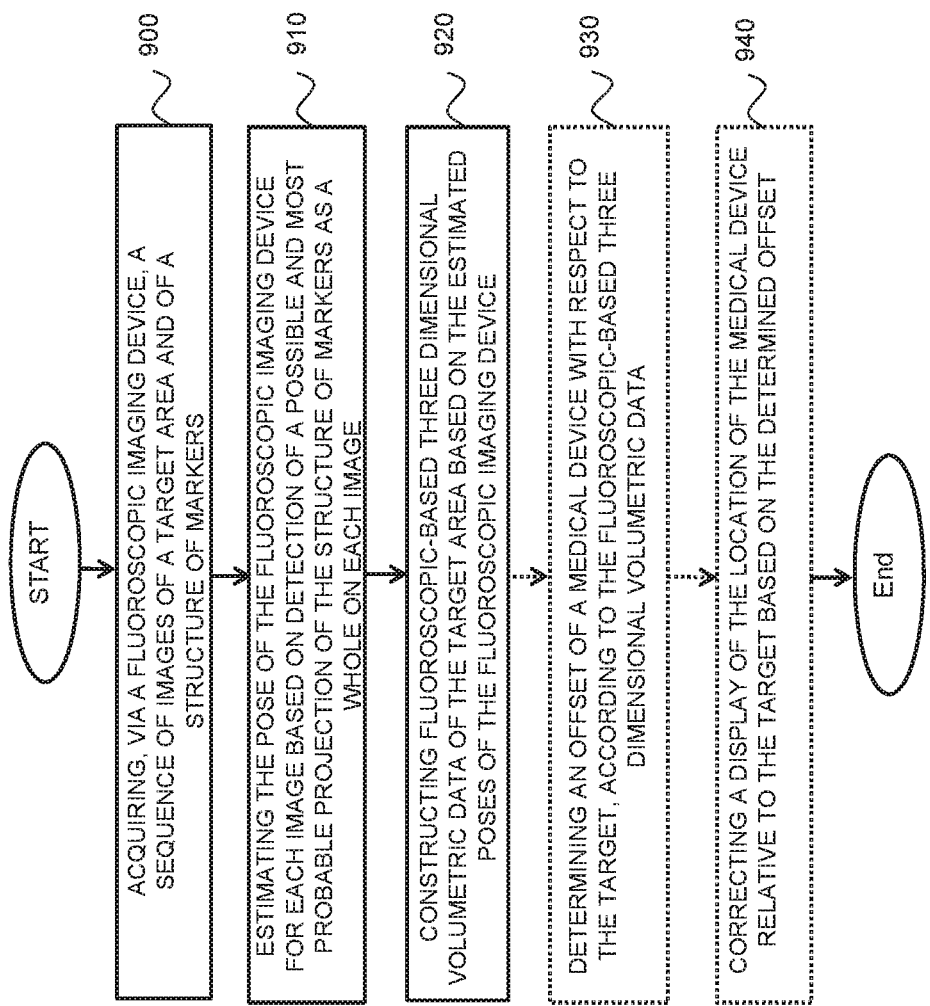
FIG. 9A is a flow chart of another method for constructing fluoroscopic three-dimensional volume via a structure of markers in accordance with the present disclosure.

In use, the three dimensional volume 205 is a portion of a patient's body. A fluoroscopic video which is comprised of multiple fluoroscope images (as frames of the video) are taken from many different locations relative to the patient, for example a 180° rotation about the patient, to acquire multiple observations of two dimensional pixels p at different positions relative to the patient. As will be described in greater detail below, the position of the fluoroscopic imaging device relative to the patient at a given time can be determined using multiple techniques, including structure-from-motion analysis of radio-opaque markers placed within the patient (FIGS. 3A-3B), a registration between the captured fluoroscopic images/video and generated virtual fluoroscopic images (FIG. 4), an external angle measurement device such as an accelerometer, gyroscope, or magnetic field sensor (FIG. 5), or by an external structure of markers (FIGS. 9A-9B). In one aspect, the system may correct for patient movements when measuring angles when a marker is utilized which moves with the movement of the body. Specifically, all of the two dimensional fluoroscopic images may be synched to the same three dimensional position based on the position of the placed marker in each of the images.

Turning now to FIGS. 3A-3B and 4-6, methods for constructing a local three dimensional volume of a target region using a standard fluoroscopic imaging device (such as the fluoroscopic imaging device 110 of FIG. 1) in conjunction with a system such as the system described in FIG. 1 will now be described with particular detail. Although the methods illustrated and described herein are illustrated and described as being in a particular order and requiring particular steps, any of the methods may include some or all of the steps and may be implemented in any order not specifically described.

The fluoroscopic-based three dimensional volume generated by any of the methods described below can be incorporated into system 100 for multiple purposes. For example, the fluoroscopic-based three dimensional volume can be registered with the previously generated three dimensional volumetric data that was utilized for navigation of the medical instrument. The system 100 may utilize the registration between the fluoroscopic-based three dimensional volume and the previously acquired three dimensional volumetric data to update the calculated position of the sensor 44 (FIG. 1) which has been placed in the body of the patient. More particularly, the three dimensional model of a patient's lungs, generated from previously acquired CT scans, may not provide a basis sufficient for accurate guiding of medical instruments to a target during an electromagnetic navigation procedure. In certain instances, the inaccuracy is caused by deformation of the patient's lungs during the procedure relative to the lungs at the time of the acquisition of the previously acquired CT data. This deformation (CT-to-Body divergence) may be caused by many different factors, for example: sedation vs. no sedation, bronchoscope changing patient pose and also pushing the tissue, different lung volume because CT was in inhale while navigation is during breathing, different bed, day, etc. Thus, another imaging modality is necessary to visualize targets and/or a terminal bronchial branch, and enhance the electromagnetic navigation procedure by correcting the navigation during the procedure, enabling visualization of the target, and confirming placement of the surgical device during the procedure. For this purpose, the system described herein processes and converts image data captured by the fluoroscopic imaging device 110, as will be described in detail below. This fluoroscopic image data may be utilized to identify such targets and terminal bronchial branches or be incorporated into, and used to update, the data from the CT scans in an effort to provide a more accurate/correction of the electromagnetic navigation procedure.

Additionally, users may visually confirm that the placement of the navigated medical instrument is positioned in a desired location relative to a target tissue within a target area. Additionally, the fluoroscopic-based three dimensional volume can be utilized to visualize the target area in three dimensions after a procedure is performed. For example, the fluoroscopic-based three dimensional volume can be utilized to visualize the target area after markers are placed within the target area, after a biopsy is taken, or after a target is treated.

Figure 3A:
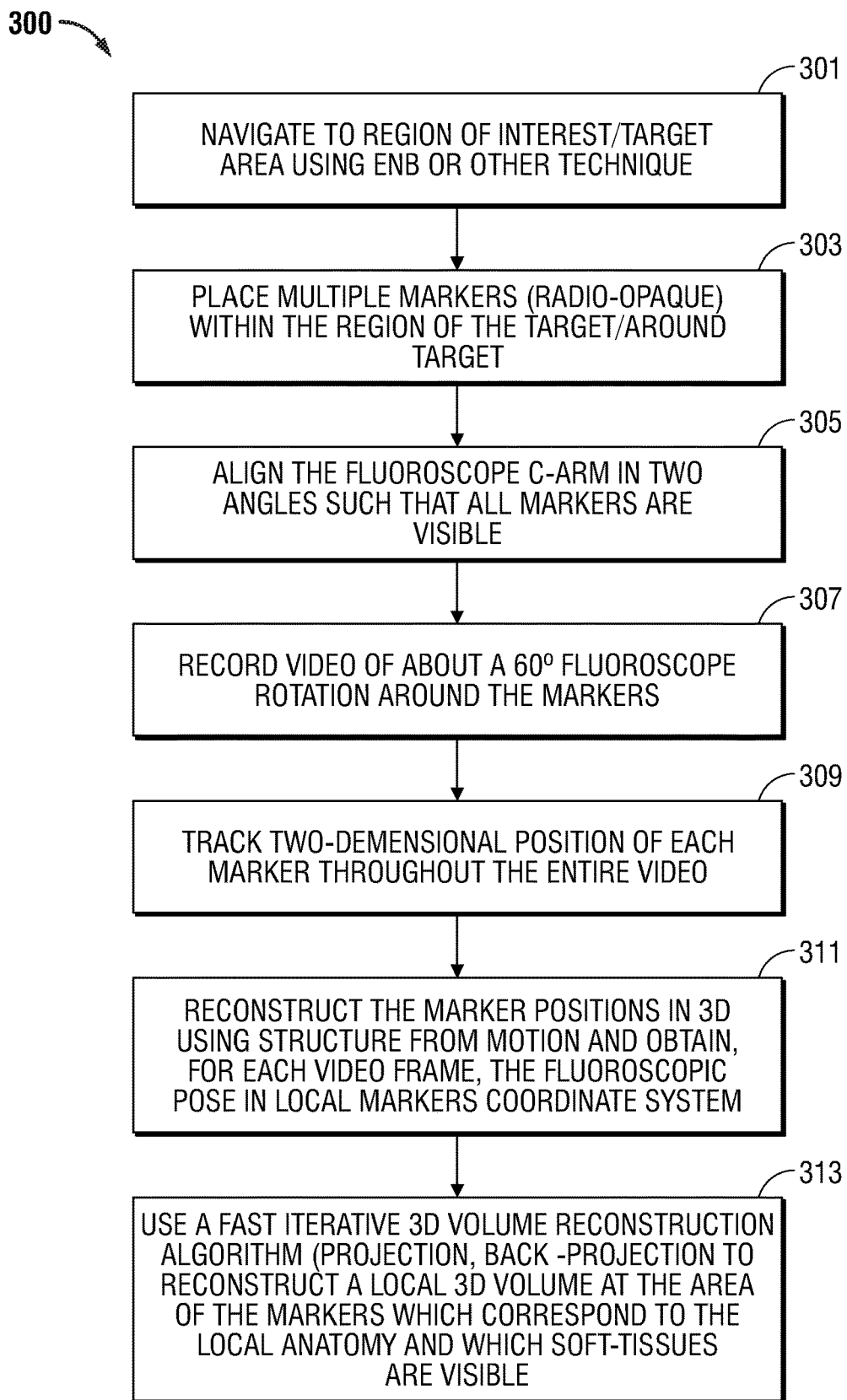
FIG. 3A is a flow chart of a method for constructing a three dimensional volume using a plurality of radio-opaque markers.
Figure 3B:
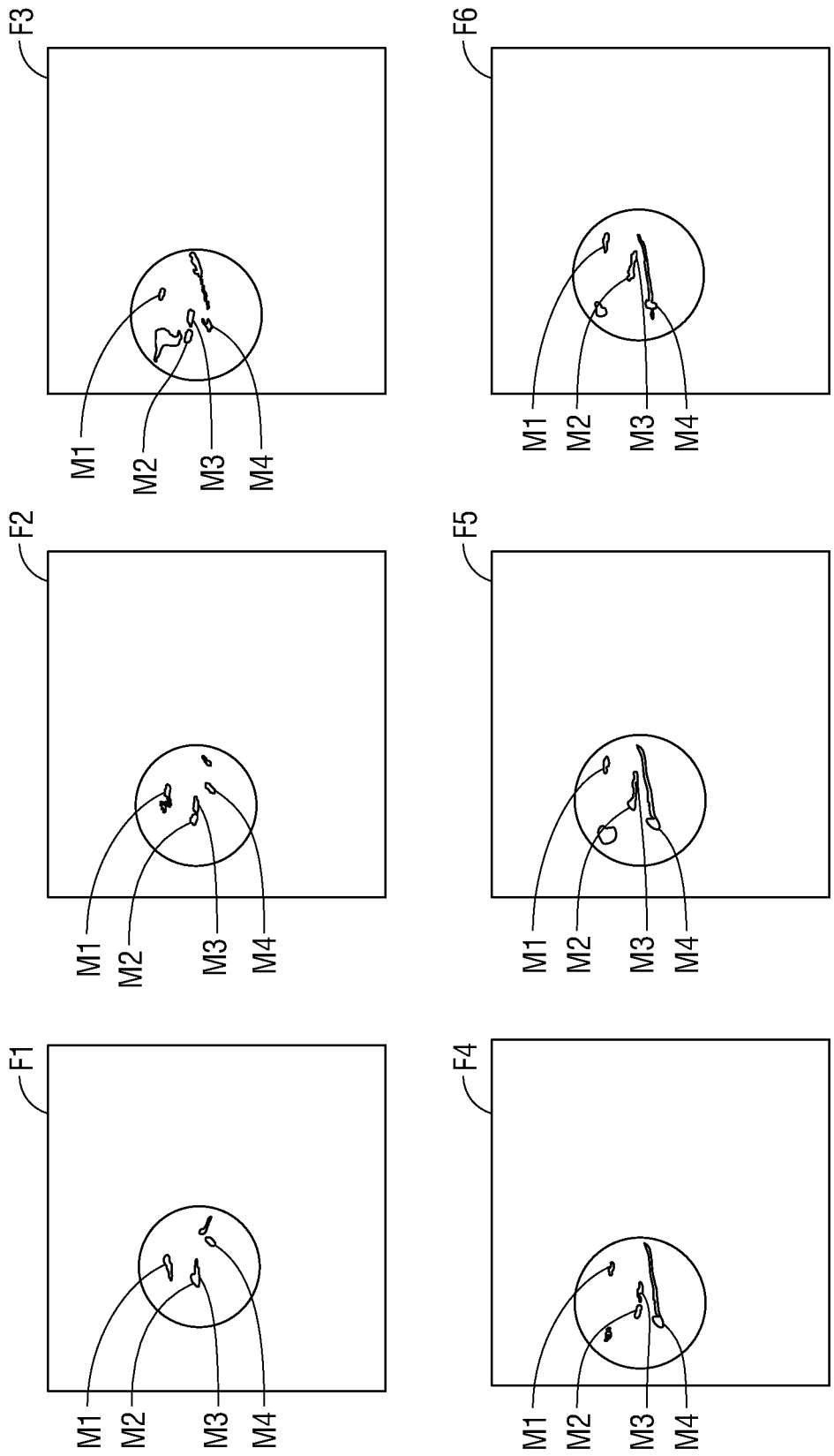
FIG. 3B is an illustration of an example of frames of a fluoroscopic video captured by a fluoroscopic imaging device showing markers and an extended working channel of a catheter assembly positioned within a target region of a patient in accordance with the instant disclosure.

With particular reference to FIGS. 3A-3B, a method for constructing a three dimensional volume using a plurality of radio-opaque markers placed proximate the target will now be described and referred to as method 300. Method 300 begins at step 301 where a marker placement device is navigated to a target area utilizing an electromagnetic navigation system, such as the EMN system 100 (FIG. 1) described above. The navigation of the marker placement device to the target area may be accomplished using a previously created navigation plan which includes routes created during the planning phase. In step 303, radio-opaque markers are placed within the target area. In one example, four radio-opaque markers are utilized. However, less than four or more than four radio-opaque markers may be used.

In step 305, with the radio-opaque markers placed in the target area, the fluoroscopic imaging device is positioned such that all of the radio-opaque markers placed in step 303 are visible. That is, step 305 includes aligning the fluoroscopic imaging device such that it can rotate 30° around the markers with all of the markers visible. In step 307, the fluoroscopic imaging device is used to capture a video of about a 30° rotation of the imaging device 110 about the patient, and thus around the markers (rotation from −15° to +15°). By rotating up to 15° (on each side) from the centered angle, it can be ensured that the markers will remain in the images/frames for the entire rotation video and that the imaging device will not hit the patient or the bed. FIG. 3B illustrates six frames f1-f6 of the captured video. Each of frames f1-f6 is an image of the fluoroscopic video showing the different position and orientation of each radio-opaque marker m1-m4 at different points in time of the video, where the fluoroscopic imaging device is positioned at a different angle relative to the patient at each given time.

In step 309, the two-dimensional position of each radio-opaque marker is tracked throughout the entire video. In step 311, the marker positions are constructed in three dimensional using structure-from-motion techniques and the pose of the fluoroscopic imaging device is obtained for each video frame. Structure-from-motion is a method for reconstructing three dimensional positions of points, along with fluoroscopic imaging device locations (camera poses) by tracking these points in a two dimensional continuous video. In step 311, by introducing markers into the patient, the positions and orientations of those markers can be tracked along a continuous fluoroscope rotation video, their three dimensional position in space can be reconstructed, and the corresponding fluoroscopic imaging device locations can be determined. With the fluoroscopic imaging device locations determined through analysis of the video, the fluoroscopic imaging device locations can be used to solve for the three dimensional data.

In step 313, a local three dimensional volume is constructed. Specifically, a fast iterative reconstruction algorithm (FIG. 6) is used to reconstruct a local three dimensional volume at the area of the markers which correspond to the local anatomy and which soft-tissues are visible. Step 313 may include reconstructing a global three dimensional volume from the acquired two dimensional fluoroscopic data and cropping the global three dimensional volume at the area of the target to create a "FluoroCT Blob" volume. This cropped volume may be displayed to the user in the form of raw three dimensional data or as two dimensional reprojected images. In this cropped volume, all anatomy in the target area, including the target tissue, will be visible. The reprojected image can be intensified (which does not include the distant dense obscuring objects) by stretching the darker value to be black and the brighter value to be white to increase differentiation and also sharpen in either three dimension before projection or in the projected images, such that the soft tissue is visually identified.

As described above, the fluoroscopic-based three dimensional volume can be incorporated into system 100 for multiple purposes. For example, the fluoroscopic-based three dimensional volume can be registered with the previously generated three dimensional volumetric data that was utilized for navigation of the medical instrument. The system 100 may utilize the registration between the fluoroscopic-based three dimensional volume and the previously acquired three dimensional volumetric data to update the calculated position of the sensor 44 (FIG. 1). Additionally, users may visually confirm that the placement of the navigated medical instrument is positioned in a desired location relative to a target tissue within a target area.

Figure 4:
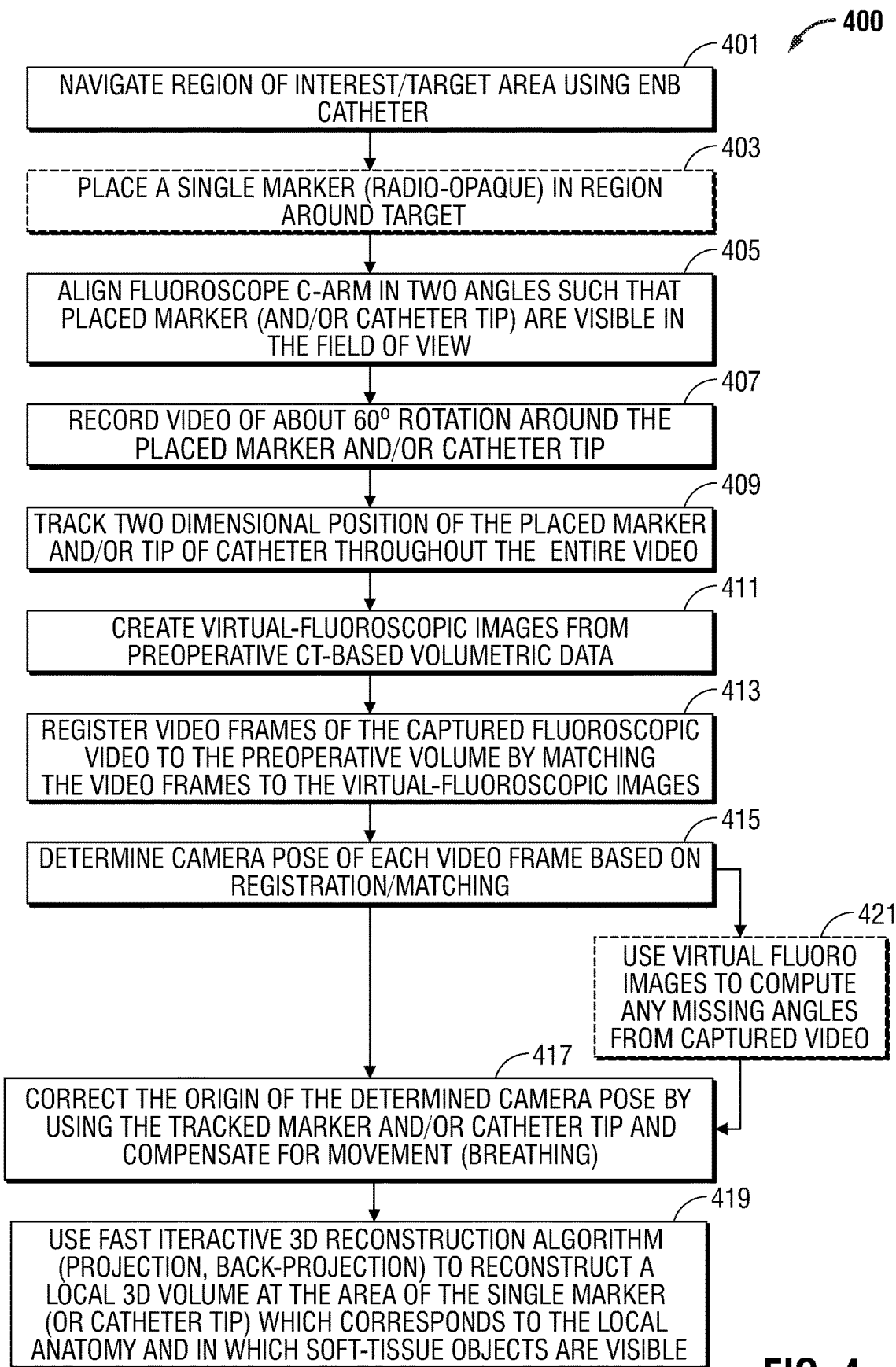
FIG. 4 is a flow chart of a method for constructing a three dimensional volume using either a single radio-opaque marker or the tip of an extended working channel of a catheter assembly.
Figure 5:
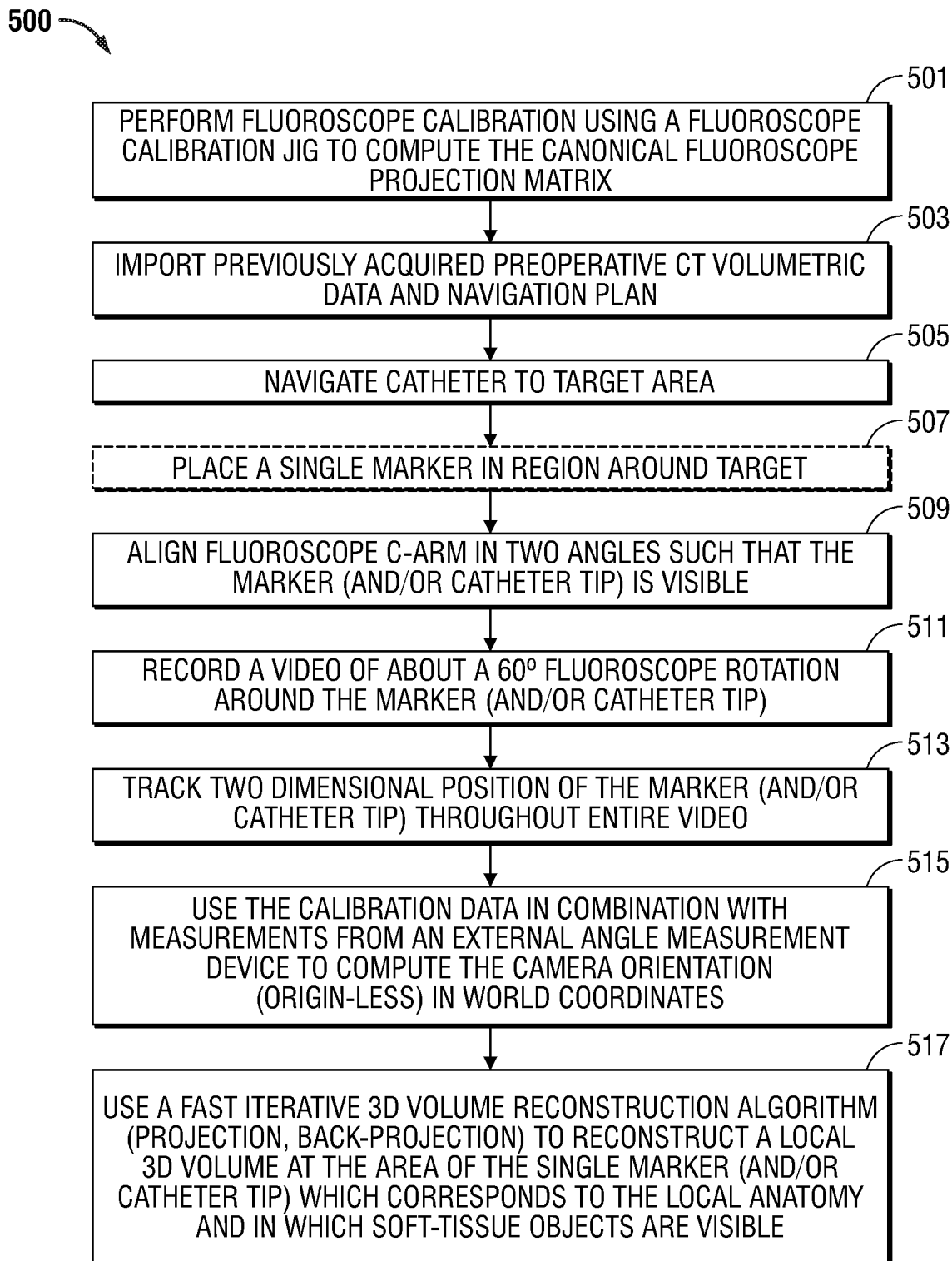
FIG. 5 is a flow chart of a method for constructing a three dimensional volume using either a single radio-opaque marker or the tip of an extended working channel of a catheter assembly in conjunction with an angle measurement device.

Turning now to FIG. 4, a method for constructing a three dimensional volume using either a single radio-opaque marker placed proximate the target or the distal portion of a navigated tool, such as the tip of the extended working channel of the catheter assembly positioned proximate the target will now be described and referred to as method 400. Although described as utilizing the tip of the extended working channel of the catheter assembly, method 400 may utilize any tool to achieve this function. For example, the tip of a navigated catheter, the tip of a biopsy tool, or the tip of a treatment tool may be utilized. In one aspect, the tool is navigated transbronchially to the target. In other aspects, the tool may be of a tool inserted into a patient percutaneously, for example, a transthoracic navigation of a treatment device such as an ablation device.

Method 400 begins at step 401 where the extended working channel is navigated to a target area utilizing an electromagnetic navigation system, such as the EMN system 100 (FIG. 1) described above. The navigation of the EWC to the target area is accomplished using a previously created navigation plan which includes routes created during the planning phase. Method 400 may optionally include the additional step of navigating a marker placement device, via the EWC, to the target area to place a single radio-opaque marker within the region of the target (step 403). In one aspect, step 401 includes percutaneously inserting a tool to the target area.

After the EWC or tool is in position, or after the radio-opaque marker is placed, the fluoroscopic imaging device is positioned such that the navigated tip of the EWC or tool (and/or the placed radio-opaque marker) is visible within the field of view of the fluoroscopic imaging device. That is, step 405 includes aligning the fluoroscopic imaging device such that it can rotate 30° around the marker with the marker visible and/or around the tip of the EWC or tool with the tip of the EWC or tool visible. In step 407, the fluoroscopic imaging device is used to capture a video of about a 30° rotation of the imaging device 110 about the patient, and thus around the marker and/or tip of the EWC or tool (rotation from −15° to +15°). By rotating up to 15° (on each side) from the centered angle, it can be ensured that the marker and/or tip of the EWC or tool will remain in the images/frames for the entire rotation video and that the imaging device will not hit the patient or the bed. Step 407 may include capturing a video of about a 30° rotation around the distal portion of the EWC (and the radio-opaque marker, if placed). If a 30° rotation video is captured, then one angle (in the middle of the range) is enough. That is, two projections with 30° between them are enough to confirm or correct three dimensional relation of tools to soft tissue.

In step 409, the two-dimensional position of the distal portion of the EWC or tool (and/or the radio-opaque marker, if placed) is tracked throughout the entire captured video.

In step 411, virtual fluoroscopic images are created from previously acquired CT data. The previously acquired CT data is typically the CT data used during the planning phase to plan a navigation path to the target. In step 411, the CT data is manipulated to create a computer model of fluoroscopic images of the patient. The location of the target in the virtual fluoroscopic images corresponds to the location of the target identified by the clinician during the planning phase. The virtual fluoroscopic images generated by the system, based off of the previously acquired CT data, depict the field of view that would be captured by a fluoroscopic imaging device. Additionally, each of the virtual fluoroscopic images has a virtual fluoroscopic imaging device pose.

In step 413, each video frame of the fluoroscopic video captured in step 407 is registered to the previously acquired CT data by matching each of the fluoroscopic video frames to the virtual fluoroscopic images. In step 415, the fluoroscopic imaging device pose of each video frame of the captured fluoroscopic video is determined based on the registration of step 413. That is, once a fluoroscopic frame is matched to a virtual fluoroscopic image, the virtual fluoroscopic imaging device pose of the virtual fluoroscopic image can be associated with the corresponding fluoroscopic frame.

In step 417, the origin of the fluoroscopic imaging device pose determined in step 415 is corrected by using the tracked position of the distal portion of the EWC or tool (and/or the radio-opaque marker, if placed), which is used to compensate for movement of the patient, such as movement caused by breathing. In step 419, a local three dimensional volume is constructed. Specifically, a fast iterative reconstruction algorithm (FIG. 6) is used to reconstruct a local three dimensional volume at the area of the target lesion which corresponds to the local anatomy and which soft-tissues are visible. Step 319 may include reconstructing a global three dimensional volume from the acquired two dimensional fluoroscopic data and cropping the global three dimensional volume at the area of the target to create a "FluoroCT Blob" volume. This cropped volume may be displayed to the user in the form of raw three dimensional data or as two dimensional reprojected images. In this cropped volume, all anatomy in the target area, including the target tissue, will be visible. The reprojected image can be intensified (which does not include the distant dense obscuring objects) by stretching the darker value to be black and the brighter value to be white to increase differentiation and also sharpen in either three dimension before projection or in the projected images, such that the soft tissue is visually identified.

Method 400 may also include the additional step (step 421) of completing the fluoroscopic video captured in step 407 to include virtual fluoroscopic images that are generated by the system, which are representative of fluoroscopic imaging device poses that are outside the range of fluoroscopic imaging device poses captured in the fluoroscopic video. Specifically, in aspects, the previously generated CT volumetric data of the patient which is used to create a navigation plan may also be utilized by system 100 to generate virtual fluoroscopic images of the patient. The generated virtual fluoroscopic images are fluoroscopic-like images which display a view to the user of what a fluoroscopic image of a patient should look like if captured at a given angle by a fluoroscopic imaging device. In step 421, the virtual fluoroscopic images may be used to fill any gaps in the captured fluoroscopic video (captured in step 407). This may include, for example, replacement of images, such as frames, of the captured video that are skewed or damaged. Additionally, or alternatively, this may include, for example, supplementing the captured fluoroscopic video (captured in step 407) with virtual fluoroscopic images that are representative of fluoroscopic images that are outside the range of angles included in the fluoroscopic video. For example, if the fluoroscopic video included a sweep of about a 30° range about the patient, virtual fluoroscopic images that are outside the 30° range could be incorporated into the video to generate a fluoroscopic video that has a range of greater than 30°.

Method 300 (FIG. 3) and method 400 (FIG. 400) are both used to construct three dimensional CT volumetric data using fluoroscopic video without knowing the fluoroscopic imaging device poses of each of the frames of the fluoroscopic video. To this end, each of methods 300 and 400 require steps of determining the fluoroscopic imaging device pose of each of the frames of the fluoroscopic video utilizing image-based techniques. In contrast, and as described in greater detail below, method 500 (FIG. 5) is a method for constructing three dimensional CT volumetric data where the fluoroscopic imaging device pose of each of the frames of the acquired fluoroscopic video are determined using a pose/angle measurement device, which may include an accelerometer, a gyroscope, or magnetic field detector to detect the position/pose of the fluoroscopic imaging device relative to the patient.

Method 500 is a method for constructing a three dimensional volume using either a single radio-opaque marker placed proximate the target or the tip of the extended working channel of the catheter assembly positioned proximate the target, in conjunction with a fluoroscope angle measurement device. Method 500 begins at step 501 where fluoroscope calibration is performed using a fluoroscope calibration jig to compute the canonical fluoroscope projection parameters and geometry. This is done once per fluoroscope device, in a setup phase by a technician. The calibration jig is used to determine, in an automated process, both the projection parameters of the fluoroscope (field of view angle) as well as the geometry of the C-arm: position relative to rotation axis. These parameters are sometimes given in technical drawings per fluoroscope device, but may also be found using our calibration jig. In step 503, the previously acquired CT volumetric data is imported into the system along with the previously generated navigation plan.

In step 505, the extended working channel is navigated to a target area utilizing an electromagnetic navigation technique using a system such as the EMN system 100 (FIG. 1) described above. The navigation of the EWC to the target area is accomplished using the previously created navigation plan which includes routes created during the planning phase. Method 500 may optionally include the additional step (step 507) of navigating a marker placement device, via the EWC, to the target area to place a single radio-opaque marker within the region of the target.

After the EWC or tool is in position, or after the radio-opaque marker is placed, method 500 proceeds to step 509 which includes aligning the fluoroscopic imaging device such that it can rotate 30° around the marker with the marker visible and/or the tip of the EWC or the tool such that the tip of the EWC or tool is visible. In step 511, the fluoroscopic imaging device is used to capture a video of about a 30° rotation of the imaging device 110 about the patient, and thus around the marker or tip of the EWC or tool (rotation from −15° to +15°). By rotating up to 15° (on each side) from the centered angle, it can be ensured that the marker or tip of the EWC or tool will remain in the images/frames for the entire rotation video and that the imaging device will not hit the patient or the bed. If a 30° rotation video is captured, then one angle (in the middle of the range) is enough. That is, two projections with 30° between them are enough to confirm or correct three dimensional relation of tools to soft tissue. In step 513, the two-dimensional position and orientation of the distal end of the EWC (and/or the radio-opaque marker, if placed) is tracked throughout the entire captured video.

In step 515, the calibration data from step 501 is utilized in combination with measurements from an external angle measurement device to compute the fluoroscopic imaging device location (origin-less) in world coordinates. Specifically, the calibration jig is used, as described above, to automatically find the projection parameters and the C-arm geometry of the specific fluoroscope device by using optimization methods. Once these parameters are known, the angle taken from the angle measurement device, that is, the angle of the detector of the fluoroscope, determines a unique three dimensional pose for the detector. It cannot be located in any other place in space other than the once explained by the given angle and the setup parameters.

In step 517, a local three dimensional volume is constructed. Specifically, a fast iterative reconstruction algorithm (FIG. 6) is used to reconstruct a local three dimensional volume at the area of the target tissue which corresponds to the local anatomy and which soft-tissues are visible. Step 517 may include reconstructing a global three dimensional volume from the acquired two dimensional fluoroscopic data and cropping the global three dimensional volume at the area of the target to create a "FluoroCT Blob" volume. This cropped volume may be displayed to the user in the form of raw three dimensional data or as two dimensional reprojected images. In this cropped volume, all anatomy in the target area, including the target tissue, will be visible. The reprojected image can be intensified (which does not include the distant dense obscuring objects) by stretching the darker value to be black and the brighter value to be white to increase differentiation and also sharpen in either three dimension before projection or in the projected images, such that the soft tissue is visually identified.

CT reconstruction methods will now be described. CT reconstruction methods can be divided into Analytic methods (Radon, FDK . . . ) and Algebraic methods (ART, SART . . . ). Analytic methods assume a very specific configuration, such as a full 180° rotation, and reconstruct the CT volume in a single iteration (using some exact formulas). Algebraic methods are more flexible but slower and treat the problem as a large equation system which is solved iteratively (using some gradient descent method). All methods use projection (three dimensional to two dimensional) and back-projection (two dimensional to three dimensional).

With respect to projection, since each detector pixel is essentially a weighted sum of three dimensional voxels along a ray, the detector image can be viewed as a two dimensional projection of the three dimensional volume from some fluoroscopic imaging device location. If the three dimensional volume data is already available, then the fluoroscope images can be reproduced by projecting it from the known fluoroscopic imaging device locations. A three dimensional reconstruction is considered good if its two dimensional projections resemble the observed fluoroscope images it was created from.

With respect to back-projection, at each voxel, the back-projection determines which rays traversed through a particular voxel and sums them together. In order to make this determination, the fluoroscopic imaging device locations must be known. If the back-projection operator were applied to the fluoroscope images of the captured video, then a three dimensional volume could be constructed, but the constructed three dimensional volume would be very blurry and inaccurate because while the true center voxel is summed many times, many irrelevant voxels surrounding the true center voxel are also summed many times. After reconstructing a three dimensional volume using one method or another, the quality of the reconstruction is evaluated by taking the reconstructed three dimensional data, projecting it into two dimensional frames (which may be virtual-fluoroscopic frames) and comparing those two dimensional frames to the original fluoroscopic two dimensional frames from which the three dimensional data was created. A goal of the volume reconstruction algorithm is to find three dimensional data which explains the two dimensional observations, such that if the three dimensional data were to be projected back into two dimensional frames, those frames would look like the original, real, fluoroscopic frames. When the product is blurry, it means that the projections are blurry and do not match the real images. In order to address this issue, the method provides for a ramp-filter and correction iteration.

Figure 6:
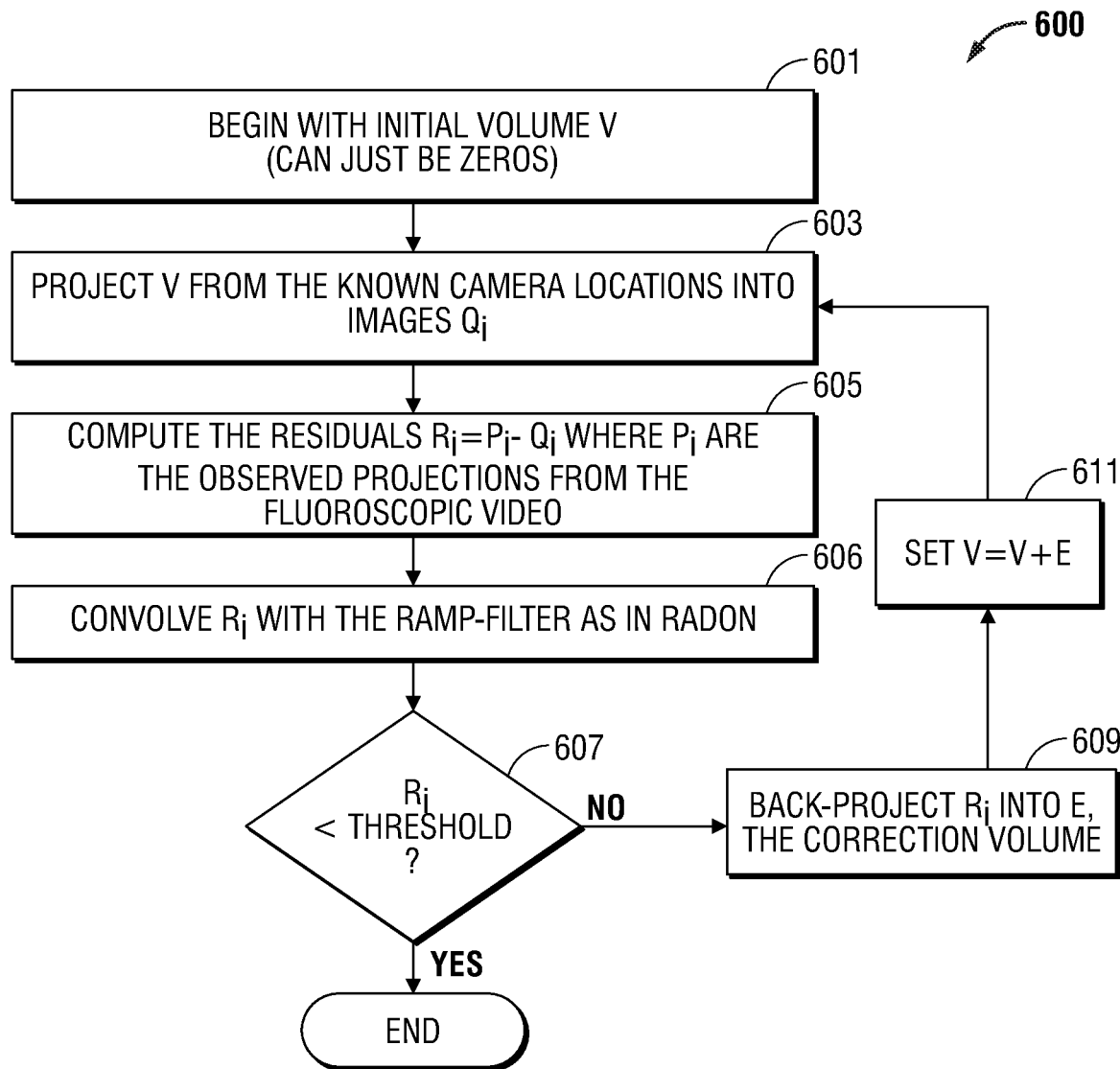
FIG. 6 is a flow chart of a method for three dimensional model construction in accordance with the instant disclosure.

Turning now to FIG. 6, a method for reconstructing a local three dimensional volume utilizing a fast iterative algorithm will now be described and referred to as method 600. The three dimensional volume reconstruction algorithm (for example method 600) consists of multiple iterations of projection—back-projection. The goal of the algorithm is to find three dimensional data which explains the two dimensional observations of the fluoroscopic imaging device. If it succeeds in finding such data then the three dimensional data found is assumed to be the three dimensional anatomy of the patient. In each iteration the current three dimensional data found is projected into two dimensions, which should look like the original fluoroscope video, then the two dimensional errors are backprojected back into the three dimensional data, and in such a manner the three dimensional data is updated. This is repeated several times until the three dimensional data converges and the process stops. In order to speed up the process, some filtering is done to the two dimensional projected images before backprojecting them back into three dimensions. The ramp-filter is just an example filter which proves to be efficient in speeding up the convergence process. This filter is applied when reconstructing standard CTs with the classic Radon transform. With the classic approach, this process is done in a single iteration: Filtering (ramp-filter for example), Back-projection. In this method, this is repeated iteratively in several steps.

Method 600 begins in step 601 where the equation begins with an initial volume V (can just be zeros). In step 603, the volume V is projected from known fluoroscopic imaging device locations into images Q. For example, projection may be done, not of the fluoroscopic images, but of the fluoroscopic images filtered by a ramp function. The iterations with residuals, described below, may undergo a ramp-filter before back-projections. In step 605, the residuals $R_i=P_iQ_i$ are computed where $P_i$ are the observed projections from the captured fluoroscope video. In step 606, $R_i$ is convolved with the ramp-filter as in Radon. In step 607, it is determined whether $R_i$ is below a predetermined threshold. If $R_i$ is below the predetermined threshold (yes in step 607), then method 600 is complete. If $R_i$ is not below the predetermined threshold (no in step 607), then method 600 proceeds to step 609. In step 609, $R_i$ is back-projected into E, the correction volume. In step 611, volume V is set to V+E (V=V+E) and method 600 reverts to step 603 where the volume V (now V+E) is projected from known fluoroscopic imaging device locations into images Q.

Figure 7:
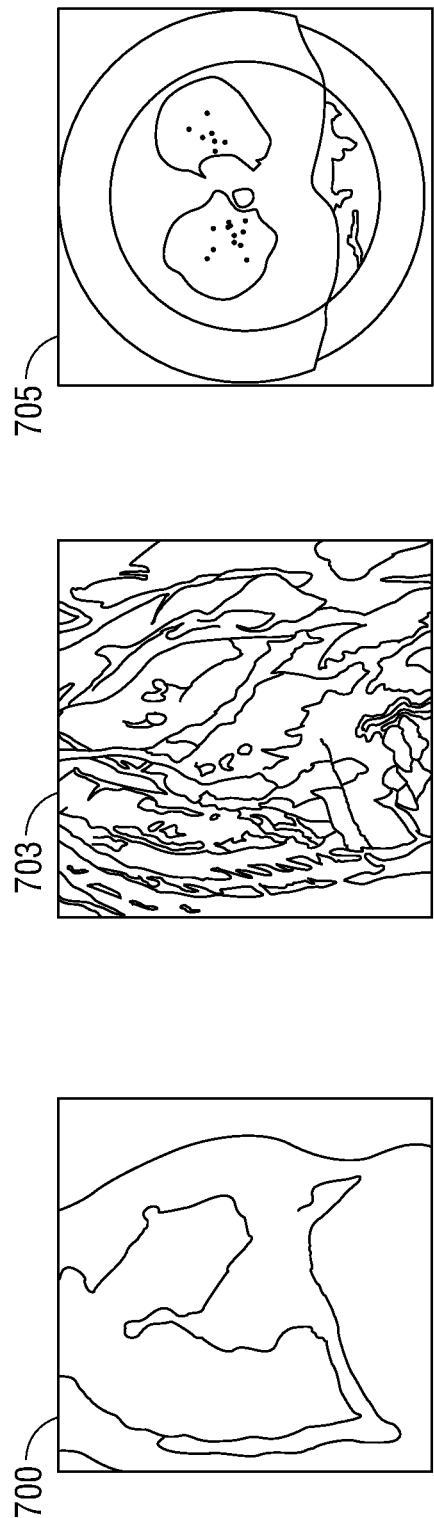
FIG. 7 is an illustration of a frame of an original video captured by a fluoroscopic imaging device, an image of the frame after being ramp filtered, and the resulting three dimensional volume.
Figure 8:
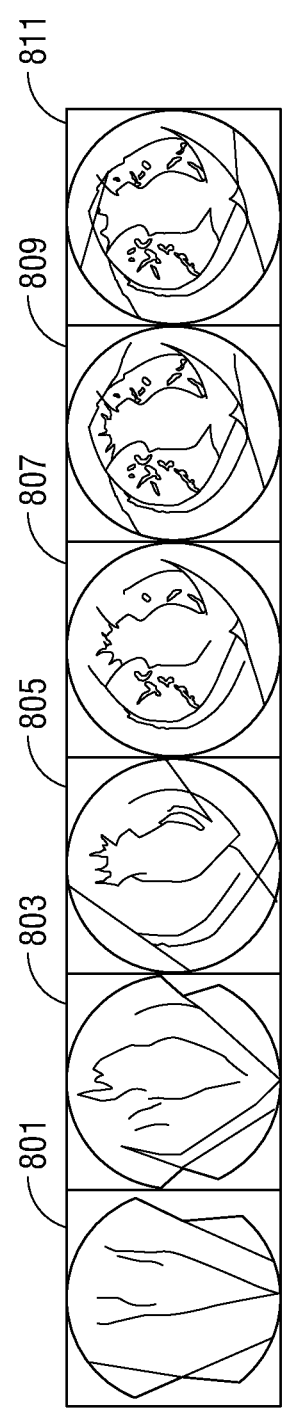
FIG. 8 is an illustration of a three dimensional construction generated according to a given angle range of fluoroscopic images/video.

Turning now to FIGS. 7 and 8. FIG. 7 illustrates a frame of an original video captured by a fluoroscopic imaging device 700, an image of the frame after being ramp-filtered 703, and an image of the resulting three dimensional volume 705. FIG. 8 is an illustration of a three dimensional construction at angles 801-88, where 801 is 30 degrees, 803 is 60 degrees, 805 is 90 degrees, 807 is 120 degrees, 809 is 150 degrees, and 811 is 180 degrees.

Reference is now made to FIG. 9A, which is a flow chart of another method for constructing fluoroscopic three-dimensional volume via a structure of markers in accordance with the present disclosure. A method for constructing fluoroscopic-based three-dimensional volumetric data of a target area within a patient from two-dimensional fluoroscopic images, is hereby disclosed. In a step 900, a sequence of images of the target area and of a structure of markers is acquired via a fluoroscopic imaging device. The structure of markers may include a plurality of at least partially radio-opaque markers arranged in a certain pattern. The structure of markers is positioned externally to the patient, e.g., under the patient, while capturing the images. The structure of markers is further positioned such that each image includes a projection of at least a portion of the structure of markers. The structure of markers may be positioned between the patient and the fluoroscopic imaging device. In some embodiments, the structure of markers may be of a two-dimensional pattern. In some embodiments, the structure of markers may be of a periodic pattern, such as a grid. In some embodiments, the target is a soft-tissue target. In some embodiments, the target area may include, for example, at least a portion of the lungs, and as exemplified with respect to the system of FIG. 1.

In a step 910, a pose of the fluoroscopic imaging device for at least a plurality of images of the sequence of images may be estimated. The pose estimation may be performed based on detection of a possible and most probable projection of the structure of markers, as a whole, on each image of the plurality of images. A probability map may be then generated for each image indicating the probability of each pixel in the image to be a marker of the structure of markers. Multiple virtual candidate for the projection of the structure of markers on the image may be generated by virtually positioning the fluoroscope in possible different locations, including possible orientations (i.e., different poses). The candidate having the highest probability of being the projection of the structure of markers on the image may be then identified based on the probability map. The virtual pose of the fluoroscope associated with the identified candidate may be then determined as the estimated pose of the fluoroscope while capturing the image. Optionally, the process of identifying a candidate may be refined. A locally deformed version of the candidate may be generated based on the probability map in order to maximize its probability of being the projection of the structure of markers on the image. A new virtual candidate may be then fitted to the locally deformed version of the identified candidate. The virtual pose of the fluoroscope which would generate the new improved candidate is the calculated and determined as the estimated pose of the fluoroscope while capturing the image. Further details with respect to the disclosed pose estimation may be found in commonly-owned U.S. patent application Ser. No. 62/628,017, entitled: "SYSTEM AND METHOD FOR POSE ESTIMATION OF AN IMAGING DEVICE AND FOR DETERMINING THE LOCATION OF A MEDICAL DEVICE WITH RESPECT TO A TARGET", filed on Feb. 8, 2018, by Barak et al., the entire content of which is hereby incorporated by reference.

In a step 920, a fluoroscopic-based three-dimensional volumetric data of the target area may be constructed based on the estimated poses of the fluoroscopic imaging device according to the disclosed systems and methods. However, other systems and methods, as known in the art, which are based on the imaging device pose information may be used.

In an optional step 930, a medical device may be positioned in the target area prior to the acquiring of the sequence of images. Thus, the sequence of images and consequently the fluoroscopic-based three-dimensional volumetric data may also include a projection of the medical device in addition to the target. The offset (i.e., Δx, Δy and Δz) between the medical device and the target may be then determined based on the fluoroscopic-based three-dimensional volumetric data. The target may be visible or better exhibited in the generated three-dimensional volumetric data. Therefore, the target may be detected, automatically, or manually by the user, in the three-dimensional volumetric data. The medical device may be detected, automatically or manually by a user, in the sequence of images, as captured, or in the generated three-dimensional volumetric data. The automatic detection of the target and/or the medical device may be performed based on systems and methods as known in the art and such as described, for example, in commonly-owned U.S. patent application Ser. No. 62/627,911, entitled: "SYSTEM AND METHOD FOR CATHETER DETECTION IN FLUOROSCOPIC IMAGES AND UPDATING DISPLAYED POSITION OF CATHETER", filed on Feb. 8, 2018, by Birenbaum et al. The manual detection may be performed by displaying to the user the three-dimensional volumetric data and/or captured images and requesting his input. Once the target and the medical device are detected in the three-dimensional volumetric data and/or the captures images, their location in the fluoroscopic coordinate system of reference may be obtained and the offset between them may be determined.

The offset between the target and the medical device may be utilized for various medical purposes, including facilitating approach of the medical device to the target area and treatment. The navigation of a medical device to the target area may be facilitated via a tracking or locating system and a display, such as tracking system 50 and monitoring equipment 120 of FIG. 1. The locating system locates or tracks the motion of the medical device through the patient's body. The display may display the medical device location to the user with respect to the surroundings of the medical device within the patient's body and the target. The locating system may be, for example, an electromagnetic or optic locating system, or any other such system as known in the art. When, for example, the target area includes a portion of the lungs, the medical device may be navigated to the target area through the airways luminal network and as described with respect to FIG. 1.

In an optional step 940, a display of the location of the medical device with respect to the target may be corrected based on the determined offset between the medical device and the target. In some embodiments, a 3D rendering of the target area may be displayed on the display. The 3D rendering of the target area may be generated based on CT volumetric data of the target area which was acquired previously, i.e., prior to the current procedure or operation (i.e., preoperative CT). In some embodiments, the locating system may be registered to the 3D rendering of the target, such as described, for example, with respect to FIG. 1. The correction of the offset between the medical device and the target may be then performed by updating the registration of the locating system to the 3D rendering. Generally, to perform such updating, a transformation between coordinate system of reference of the fluoroscopic images and the coordinate system of reference of the locating system should be known. The geometrical positioning of the structure of markers with respect to the locating system may determine such a transformation. In some embodiments the structure of markers and the locating system may be positioned such that the same coordinate system of reference would apply to both, or such that the one would be only a translated version of the other. For example, and with reference to FIG. 1, transmitter mat 56 may be incorporated with the structure of markers.

In some embodiments, the updating of the registration of the locating system to the 3D rendering (e.g., CT-based) may be performed in a local manner and/or in a gradual manner. For example, the registration may be update only in the surroundings of the target, e.g., only within a certain distance from the target. This is since the update may be less accurate when not performed around the target. In some embodiments, the updating may be performed in a gradual manner, e.g., by applying weights according to distance from the target. In addition to accuracy considerations, such gradual updating may be more convenient or easier for the user to look at, process and make the necessary changes during procedure, than abrupt change in the medical device location on the display.

In some embodiments, the patient may be instructed to stop berating during the capture of the images in order to prevent movements of the target area due to breathing. In other embodiments, methods for compensating breathing movements during the capture of the images may be performed. For example, the estimated poses of the fluoroscopic device may be corrected according to the movements of a fiducial marker placed in the target area. Such a fiducial may be a medical device, e.g., a catheter, placed in the target area. The movement of the catheter, for example, may be determined based on the locating system. In some embodiments, a breathing pattern of the patient may be determined according to the movements of a fiducial marker, such as a catheter, located in the target area. The movements may be determined via a locating system. Based on that pattern, only images of inhale or exhale may be considered when determining the pose of the imaging device.

Reference is now made to FIG. 9B, which is a schematic illustration of a two-dimensional (2D) grid structure of sphere markers 950, in accordance with the method of FIG. 9A. 2D grid structure of sphere markers 950 includes a plurality of sphere shaped markers, such as sphere markers 960a and 960b, arranged in a two-dimensional grid pattern. Using a 2D pattern, as opposed to a 3D pattern, may facilitate the pose estimation process. Furthermore, when for example, a patient is required to lie on the markers structure in order to estimate the pose of the fluoroscope while scanning the patient, a 2D pattern would be more convenient for the patient. In some embodiments, the shape of the markers may be symmetric and such that the projection of the markers on the image would be the same at any pose of the imaging device may be placed. Such configuration may simplify and enhance the pose estimation process and/or make it more efficient. For example, when the imaging device is rotated around the markers structure, markers having a rotation symmetry may be preferred, such as spheres. The size of the markers structure and/or the number of markers in the structure may be determined according to the specific use of the disclosed systems and methods. For example, since the pose estimation is used to construct a 3D volume of an area of interest within a patient, then the markers structure may be of a size similar or larger than the size of the area of interest. In some embodiments, the pattern of a structure of markers according to the disclosed methods and systems may be periodic, such as a grid, as shown in FIG. 2A. Using a periodic pattern structure of markers may further enhance and facilitate the pose estimation process and make it more efficient. The structure of markers, as a fiducial, should be positioned in a stationary manner during the capturing of the fluoroscopic images. In an exemplary 2D grid structure of sphere markers, which may be used in conjunction with the system of FIG. 1, the sphere markers diameter may be 2±0.2 mm and the distance between the spheres may be about 15±0.15 mm isotropic.

The system of FIG. 1 may be configured to execute the method of FIG. 9A. The method of FIG. 9A, or a portion of it, may be in the form of instructions executed by a computing device, such as computing device 125 of FIG. 1. The computing device may include one or more hardware processors, one or more memories or storage devices and a display. The one or more hardware processors may be configured to execute the steps of this method. The one or more memories or storage devices may be configured to store these instruction and/or the fluoroscopic image data. The medical device and/or target may be displayed on the display or on a separate monitor such as monitoring equipment 10 of FIG. 1.

From the foregoing and with reference to the various figure drawings, those skilled in the art will appreciate that certain modifications can also be made to the present disclosure without departing from the scope of the same. For example, although the systems and methods are described as usable with an EMN system for navigation through a luminal network such as the lungs, the systems and methods described herein may be utilized with systems that utilize other navigation and treatment devices such as percutaneous devices. Additionally, although the above-described system and method is described as used within a patient's luminal network, it is appreciated that the above-described systems and methods may be utilized in other target regions such as the liver, kidney or heart. Further, the above-described systems and methods are also usable for transthoracic needle aspiration procedures. Additionally, although the above-described system and method is described as used mainly with respect to soft-tissue targets, it is appreciated that the above-described systems and methods may be utilized with respect to non-soft-tissue targets, such as bones. Furthermore, the above-described systems and methods are also usable with robotic surgery systems, such as da Vinci® Surgical System currently sold by Intuitive Surgical®. For example, and with reference to FIG. 1, system 100 may be such a robotic surgery system. Operating table 20, on which the patient is positioned during surgery, may be incorporate in a cart including one or more robotic arms. The one or more robotic arms may be coupled with one or more dedicated medical devices. Monitoring equipment 120 and/or computing device 125 may be incorporate in a controller, e.g., a computerized console, allowing the surgeon to operate the one or more robotic arms while viewing the inside of the patient. Detailed embodiments of the present disclosure are disclosed herein. However, the disclosed embodiments are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As can be appreciated a medical instrument such as a biopsy tool or an energy device, such as a microwave ablation catheter, that is positionable through one or more branched luminal networks of a patient to treat tissue may prove useful in the surgical arena and the present disclosure is directed to systems and methods that are usable with such instruments and tools. Access to luminal networks may be percutaneous or through natural orifice using navigation techniques. Additionally, navigation through a luminal network may be accomplished using image-guidance. These image-guidance systems may be separate or integrated with the energy device or a separate access tool and may include MRI, CT, fluoroscopy, ultrasound, electrical impedance tomography, optical, and/or device tracking systems. Methodologies for locating the access tool include EM, IR, echolocation, optical, and others. Tracking systems may be integrated to an imaging device, where tracking is done in virtual space or fused with preoperative or live images. In some cases the treatment target may be directly accessed from within the lumen, such as for the treatment of the endobronchial wall for COPD, Asthma, lung cancer, etc. In other cases, the energy device and/or an additional access tool may be required to pierce the lumen and extend into other tissues to reach the target, such as for the treatment of disease within the parenchyma. Final localization and confirmation of energy device or tool placement may be performed with imaging and/or navigational guidance using a standard fluoroscopic imaging device incorporated with methods and systems described above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for constructing fluoroscopic-based three-dimensional volumetric data of a target area within a patient from two-dimensional fluoroscopic images, comprising:
    a structure of markers; and
    a computing device configured to:
        receive a sequence of fluoroscopic images of the target area captured by a fluoroscopic imaging device, each image comprising at least a portion of the structure of markers;
        estimate a pose of the fluoroscopic imaging device for a plurality of images of the sequence of fluoroscopic images based on detection of a projection of the structure of markers on each image of the sequence of images;
        construct fluoroscopic-based three-dimensional volumetric data of the target area based on each estimated pose of the fluoroscopic imaging device, the fluoroscopic-based three-dimensional volumetric data of the target area including a medical device and a target; and
        analyze the constructed fluoroscopic-based three-dimensional volumetric data to determine an offset between a location of the medical device within the constructed fluoroscopic-based three-dimensional volumetric data of the target area and a location of the target within the constructed fluoroscopic-based three-dimensional volumetric data of the target area.

2. The system of claim 1, wherein the computing device is further configured to facilitate an approach of the medical device to the target.

3. The system of claim 1, further comprising a locating system configured to determine the location of the medical device within the patient, wherein the computing device comprises a display and is configured to:
    display the target area and the location of the medical device with respect to the target based on the location of the medical device as determined by the locating system;
    facilitate navigation of the medical device to the target area via the locating system and the display; and
    correct the display of the location of the medical device with respect to the target based on the determined offset between the location of the medical device within the constructed fluoroscopic-based three-dimensional volumetric data and the location of the target within the constructed fluoroscopic-based three-dimensional volumetric data as determined by the computing device based on the constructed fluoroscopic-based three-dimensional volumetric data of the target area.

4. The system of claim 3, wherein the computing device is further configured to:
    display a 3D rendering of the target area on the display; and
    register the locating system to the 3D rendering,
    wherein the display of the location of the medical device with respect to the target is corrected by updating a registration between the locating system and the 3D rendering.

5. The system of claim 3, wherein the locating system is an electromagnetic locating system.

6. The system of claim 3, wherein the target area comprises at least a portion of lungs and the medical device is navigated to the target area through a luminal network.

7. The system of claim 1, wherein structure of markers is of a periodic pattern.

8. The system of claim 1, wherein structure of markers is of a two-dimensional pattern.

9. The system of claim 1, wherein the target is a soft-tissue target.

10. A method for constructing fluoroscopic-based three dimensional volumetric data of a target area within a patient from two dimensional fluoroscopic images, the method comprising using at least one hardware processor for:
    acquiring, via a fluoroscopic imaging device, a sequence of images of the target area, each image comprising at least a portion of a structure of markers, wherein the structure of markers is positioned between the patient and the fluoroscopic imaging device;
    estimating a pose of the fluoroscopic imaging device for a plurality of images of the sequence of images based on detection of a projection of the structure of markers on each image of the sequence of images;
    constructing fluoroscopic-based three-dimensional volumetric data of the target area based on each estimated pose of the fluoroscopic imaging device, the fluoroscopic-based three-dimensional volumetric data of the target area including a medical device and a target in the target area; and
    analyzing the constructed fluoroscopic-based three-dimensional volumetric data to determine an offset between a location of the medical device within the constructed fluoroscopic-based three-dimensional volumetric data of the target area and a location of the target within the constructed fluoroscopic-based three-dimensional volumetric data of the target area.

11. The method of claim 10, wherein the medical device is positioned in the target area prior to the acquiring of the sequence of images.

12. The method of claim 11, further comprising using said at least one hardware processor for:
    determining the location of the medical device via a locating system;
    facilitating navigation of the medical device to the target area via the locating system indicating the location of the medical device and via a display; and
    correcting a display of the location of the medical device with respect to the target based on the determined offset between the location of the medical device within the constructed fluoroscopic-based three-dimensional volumetric data and the location of the target within the constructed fluoroscopic-based three-dimensional volumetric data based on the constructed fluoroscopic-based three-dimensional volumetric data of the target area.

13. The method of claim 12, further comprising using said at least one hardware processor for:
   displaying a 3D rendering of the target area on the display; and
   registering the locating system to the 3D rendering,
   wherein the correcting of the display of the location of the medical device with respect to the target comprises updating a registration of the locating system to the 3D rendering.

14. The method of claim 13, further comprising using said at least one hardware processor for generating the 3D rendering of the target area based on previously acquired CT volumetric data of the target area.

15. The method of claim 12, wherein the locating system is an electromagnetic locating system.

16. The method of claim 12, wherein the target area comprises at least a portion of lungs and wherein the medical device is navigated to the target area through a luminal network.

17. The method of claim 12, wherein the structure of markers is of a periodic pattern.

18. The method of claim 12, wherein the structure of markers is of a two-dimensional pattern.

19. The method of claim 12, wherein the target is a soft-tissue target.

20. A system for constructing fluoroscopic-based three-dimensional volumetric data of a target area within a patient from two-dimensional fluoroscopic images, comprising:
   a computing device configured to:
      receive a sequence of fluoroscopic images of the target area captured by a fluoroscopic imaging device;
      estimate a pose of the fluoroscopic imaging device for a plurality of images of the sequence of fluoroscopic images;
      construct fluoroscopic-based three-dimensional volumetric data of the target area based on each estimated pose of the fluoroscopic imaging device, the fluoroscopic-based three-dimensional volumetric data of the target area including a medical device and a target; and
      analyze the constructed fluoroscopic-based three-dimensional volumetric data to determine an offset between a location of the medical device within the constructed fluoroscopic-based three-dimensional volumetric data of the target area and a location of the target within the constructed fluoroscopic-based three-dimensional volumetric data of the target area.

* * * * *